United States Patent
Sieben et al.

(10) Patent No.: US 10,031,122 B2
(45) Date of Patent: Jul. 24, 2018

(54) AUTOMATED METHOD AND APPARATUS TO CHARACTERIZE SOLUBILITY OF ASPHALTENES OF A HYDROCARBON FLUID SAMPLE UTILIZING MICROFLUIDICS

(71) Applicant: SCHLUMBERGER TECHNOLOGY CORPORATION, Sugar Land, TX (US)

(72) Inventors: Vincent Joseph Sieben, Edmonton (CA); Simon Ivar Andersen, Copenhagen (DK); Farshid Mostowfi, Edmonton (CA); Abdel M. Kharrat, Edmonton (CA)

(73) Assignee: SCHLUMBERGER TECHNOLOGY CORPORATION, Sugar Land, TX (US)

(*) Notice: Subject to any disclaimer, the term of this patent is extended or adjusted under 35 U.S.C. 154(b) by 17 days.

(21) Appl. No.: 14/893,016

(22) PCT Filed: May 28, 2014

(86) PCT No.: PCT/US2014/039800
§ 371 (c)(1),
(2) Date: Nov. 20, 2015

(87) PCT Pub. No.: WO2015/023343
PCT Pub. Date: Feb. 19, 2015

(65) Prior Publication Data
US 2016/0097757 A1 Apr. 7, 2016

Related U.S. Application Data
(60) Provisional application No. 61/864,987, filed on Aug. 12, 2013.

(51) Int. Cl.
*G01N 31/00* (2006.01)
*G01N 33/28* (2006.01)
(Continued)

(52) U.S. Cl.
CPC ........ *G01N 33/2835* (2013.01); *B01L 3/5027* (2013.01); *G01N 1/28* (2013.01);
(Continued)

(58) Field of Classification Search
None
See application file for complete search history.

(56) References Cited

U.S. PATENT DOCUMENTS

| 7,736,900 B2 | 6/2010 | Pauli et al. |
| 2004/0012782 A1 | 1/2004 | Mason et al. |

(Continued)

OTHER PUBLICATIONS

Andersen, S. I. Flocculation Onset Titration of Petroleum Asphaltenes, 2009, Energy & Fuels, vol. 13(2), pp. 315-322.*

(Continued)

*Primary Examiner* — Xiaoyun R Xu

(57) ABSTRACT

A method and apparatus for analyzing solubility of asphaltenes of a hydrocarbon fluid sample involves a sequence of operations including: i) performing microfluidic mixing operations that form a mixture that includes the hydrocarbon fluid sample, a solvent that dissolves asphaltenes and a precipitant that precipitates asphaltenes; ii) using microfluidic processes that result in precipitation of asphaltenes from the mixture resulting from i); iii) performing microfluidic filtering operations that remove precipitated asphaltenes resulting from ii) and passes permeate; and iv) performing optical spectroscopy on the permeate resulting from iii). The operations of i)-iv) can be repeated over iterations that vary the amount of solvent relative to the precipitant in the mixture. These iterations can cause varying (Continued)

fractional precipitation of asphaltenes in each given iteration.

25 Claims, 12 Drawing Sheets

(51) Int. Cl.
| | |
|---|---|
| *G01N 1/28* | (2006.01) |
| *G01N 33/24* | (2006.01) |
| *G01N 33/42* | (2006.01) |
| *G01N 21/31* | (2006.01) |
| *G01N 1/40* | (2006.01) |
| *B01L 3/00* | (2006.01) |
| *G01N 21/82* | (2006.01) |
| *G01N 1/38* | (2006.01) |

(52) U.S. Cl.
CPC ........... *G01N 1/4055* (2013.01); *G01N 21/31* (2013.01); *G01N 21/82* (2013.01); *G01N 33/24* (2013.01); *G01N 33/42* (2013.01); *G01N 2001/381* (2013.01); *G01N 2001/4061* (2013.01); *G01N 2201/12* (2013.01)

(56) References Cited

U.S. PATENT DOCUMENTS

| | | | |
|---|---|---|---|
| 2011/0062058 A1 | 3/2011 | Rogel et al. | |
| 2011/0292382 A1* | 12/2011 | Mostowfi | G01N 33/2823 356/246 |
| 2012/0160015 A1 | 6/2012 | Ovalles et al. | |

OTHER PUBLICATIONS

Akbarzadeh, K., "A Generalized Regular Solution Model for Asphaltene Precipation from n-Alkane Diluted Heavy Oils and Bitumens", Fluid Phase Equilibria, vol. 232, Issues 1-2, May 25, 2005, pp. 159-170.
Alboudwarej, H., "Regular Solution Model for Asphaltene Precipitation from Bitumens and Solvents", AIChE Journal, vol. 49, No. 11, Nov. 2003, pp. 2948-2956.
Andersen, Simon Ivar, "Flocculation Onset Titration of Petroleum Asphaltenes", American Chemical Society, (1999) pp. 315-322.
Andersen, Simon I et al., Thermodynamic Models for Asphaltene Solubility and Precipitation, Journal of Petroleum Science and Engineering, vol. 22 (1999) pp. 53-66.
Heithaus, J.J. et al, "Measurement and Significance of Asphaltene Peptization", American Chemical Society, Sep. 1960, pp. A-23-A-37.
Hirschberg, A. et al., "Influence of Temperature and Pressure on Asphaltene Flocculation", Society of Petroleum Engineers of AIME, Jun. 1984, pp. 283-293.
Knox, John H., "Band Dispersion in Chromatography—a Universal Expression for the Contribution From the Mobile Zone", Journal of Chromatography A, vol. 960 (2002) pp. 7-18.
Mannistu, K.D. et al., "Solubility Modeling of Asphaltenes in Organic Solvents", American Chemical Society, (1997) pp. 615-622.
Mitchell, David, L., et al., "The Solubility of Asphaltenese in Hydrocarbon Solvents", Fuel, vols. 52 (1973) pp. 149-152.
Nguyen, Nam-Trung et al., "Micromixers—A Review", J. Micromech. Microeng., vol. 15 (2005) pp. R1-R16.
Nikooyeh, Kasra et al., "On the Applicability of the Regular Solution Theory to Asphaltene + Diluent Mixtures", Energy & Fuels, vol. 26, (2012) pp. 576-585.
O. Sabbagh, K. Akbarzadeh et al., "Applying the PR-EoS to Asphaltene Precipitation from n-Alkane Diluted Heavy Oils and Bitumens", Energy & Fuels, vol. 20, (2006) pp. 625-634.
Pauli, Adam T., "Asphalt Compatibility Testing Using the Automated Heithaus Titration Test", ACS Division of Fuel Chemistry Preprints, 41(4), (1996) pp. 1276-1280.
Rogel, Estrella et al., "Asphaltene Stability in Crude Oils and Petroleum Materials by Solubility Profile Analysis", Journal of Colloid and Interface Science, 267(1), (2010) pp. 178-193.
Schneider, Marc H. et al., "Measurement of Asphaltenes Using Optical Spectroscopy on a Microfluidic Platform", Anal. Chem. (2013) vol. 85, pp. 5153-5160.
Spiecker, Matthew P., et al., "Aggregation and Solubility Behavior of Asphaltenes and Their Subfractions", Journal of Colloid and Interface Science, vol. 267 (2003) pp. 178-193.
Wattana, Piyarat et al., "Characterization of Polarity-Based Asphaltene Subfractions", Energy & Fuels, (2005), vol. 19, pp. 101-110.
Wiehe, Irwin A., "Asphaltene Solubility and Fluid Compatibility", Energy and Fuels, 26(7), (2012) pp. 4004-4016.
Yarranton, Harvey W. et al., "Molar Mass Distribution and Solubility Modeling of Asphaltenes", AIChE Journal, 42(12), (1996) pp. 3533-3543.

* cited by examiner

AUTOMATED METHOD AND APPARATUS TO CHARACTERIZE SOLUBILITY OF ASPHALTENES OF A HYDROCARBON FLUID SAMPLE UTILIZING MICROFLUIDICS

CROSS-REFERENCE TO RELATED APPLICATION(S)

The present application claims priority from U.S. Provisional Patent Application 61/864,987, filed Aug. 12, 2013, herein incorporated by reference in its entirety.

BACKGROUND

Field

The present application relates to methods and apparatus for characterizing the solubility of asphaltenes of a hydrocarbon fluid sample.

Related Art

Solubility analysis is used in the petroleum industry as a guideline to evaluate the stability and compatibility of the oil constituents of a reservoir fluid sample, often when the sample is mixed with diluents or when comingled with other oil mixtures as described in Nikooyeh, K. and Shaw, J. M., "On the Applicability of the Regular Solution Theory to Asphaltene and Diluent Mixtures," *Energy & Fuels*, Vol. 26(1), 2011, pp. 576-585 and in Wiehe, I. A., "Process Chemistry of Petroleum Macromolecules. Chemical Industries", Taylor & Francis, 2008. The regular solution theory is commonly described as "like dissolves like" and states that two compounds with close solubility parameters are likely to be mutually miscible.

In particular, solubility analysis is used in the petroleum industry to study the asphaltene component of oil that can precipitate upon a change in pressure, temperature, or composition of the oil mixture; generally attributed to a variation in the solubility matrix. In fact, asphaltenes are typically defined as a solubility class of material, being poorly soluble in alkanes (e.g. n-heptane) and highly soluble in aromatic solvents (e.g. toluene). Asphaltene solubility parameters, calculated and/or measured, are used as inputs to many modeling approaches that predict asphaltene behavior when crude oils undergo physical and or chemical changes as described in Alboudwarej, H. et al., "Regular Solution Model for Asphaltene Precipitation from Bitumens and Solvents," *AIChE Journal*, Vol. 49(11), 2003, pp. 2948-2956, and Hirschberg, A. et al., "Influence of Temperature and Pressure On Asphaltene Flocculation", *Society of Petroleum Engineers Journal*, Vol. 24(3), 1984, pp. 283-293 and Andersen, S. I., and Speight, J. G., "Thermodynamic Models for Asphaltene Solubility and Precipitation", *Journal of Petroleum Science and Engineering* 22, no. 1-3 (1999): pp. 53-66. The precipitation and deposition of asphaltenes from reservoir fluids during production, transportation, sample handling, and processing of reservoir fluids is a major impediment with associated costs on the order of billions worldwide as described in Rogel, E., Ovalles, C. and Moir, M., "Asphaltene Stability in Crude Oils and Petroleum Materials by Solubility Profile Analysis", *Energy & Fuels*, Vol. 24(8), 2010, pp. 4369-4374. Optimal flow assurance requires that models accurately predict asphaltene behavior in order to identify and avoid problematic conditions. Therefore, consistent and reliable measurement techniques that report asphaltene solubility profiles are useful for managing these production problems.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

Illustrative embodiments of the present disclosure are directed to a method and apparatus of analyzing solubility of asphaltenes of a hydrocarbon fluid sample. The method (and corresponding apparatus) involves a sequence of operations including i) performing microfluidic mixing operations that form a mixture that includes the hydrocarbon fluid sample, a solvent fluid that dissolves asphaltenes, and a precipitant fluid that precipitates asphaltenes;

ii) using microfluidic processes that result in precipitation of asphaltenes as part of the mixture resulting from i);

iii) performing microfluidic filtering operations that remove precipitated asphaltenes from the mixture that results from ii) and passes on permeate; and iv) performing optical spectroscopy on the permeate resulting from iii).

In one embodiment, the operations of i)-iv) are repeated over a number of iterations that vary the amount of solvent fluid relative to the precipitant fluid in the mixture that results from i). Specifically, the iterations can vary the volume fraction of the solvent fluid relative to the precipitant fluid in the mixture that results from i) in each given iteration. These iterations can cause varying fractional precipitation of asphaltenes during the operations of ii) in each given iteration.

The sequence of operations of the methodology can also include the following:

v) performing microfluidic mixing operations that form a mixture that includes the hydrocarbon fluid sample and the solvent fluid, but does not include the precipitant fluid;

vi) using microfluidic processes that result in dissolution of asphaltenes as part of the mixture resulting from v);

vii) performing microfluidic filtering operations that remove precipitated asphaltenes from the mixture that results from vi), if any, and passes on permeate; and viii) performing optical spectroscopy on the permeate resulting from vii).

The sequence of operations of the methodology can also include the following:

ix) performing microfluidic mixing operations that form a mixture that includes the hydrocarbon fluid sample and the precipitant fluid, but does not include the solvent fluid;

x) using microfluidic processes that result in precipitation of asphaltenes as part of the mixture resulting from ix);

xi) performing microfluidic filtering operations that remove precipitated asphaltenes from the mixture that results from x) and passes on permeate; and xii) performing optical spectroscopy on the permeate resulting from xi).

The microfluidic mixing operations of i), the microfluidic processes of ii), and the microfluidic filtering operations of iii) can be performed by at least one microfluidic chip. In one embodiment, the at least one microfluidic chip includes first and second input ports that are fluidly coupled to a mixer section. The first input port supplies a combination of the solvent fluid and the precipitant fluid to the mixer section for use in conjunction with the microfluidic mixing operations of i). The second input port supplies the hydrocarbon fluid sample fluid to the mixer section for use in conjunction with the microfluidic mixing operations of i). The at least one microfluidic chip can also include a reactor section fluidly coupled downstream from the mixer section. The at least one microfluidic chip can also include a membrane filter section fluidly coupled downstream from the reactor section. The membrane filter section can lead to both a waste port and an outlet port. In another embodiment, the microfluidic mixing operations of i) and the microfluidic processes of ii) are performed by a first microfluidic chip, and the microfluidic filtering operations of iii) are performed by a second microfluidic chip that is separate and distinct from the first microfluidic chip and fluidly coupled to the first microfluidic chip. A flow-through optical cell can be fluidly coupled between the first microfluidic chip and the second microfluidic chip, and the flow-through optical cell can be optically coupled to a corresponding spectrometer.

The optical spectroscopy of iv) can involve the permeate resulting from iii) passing through a flow-through optical cell, wherein the flow-through optical cell is optically coupled to a corresponding spectrometer.

The operations of i) to iv) can be part of an automated workflow.

The hydrocarbon fluid sample can be, for example, a crude oil, a blend of different crude oils, one or more additives combined with crude oil, coal liquefaction products, mixtures of naphtha and bitumen, mixtures of refinery residua and diluents, and road asphalts. The hydrocarbon fluid may also comprise unconventional oils, shale oil, and diluted bitumen, or blends of any of these.

The methodology can be extended to derive and store an optical spectrum measurement during the optical spectroscopy of iv) over a number of iterations that vary the amount of solvent fluid relative to the precipitant fluid in the mixture that results from i) in each given iteration. The stored optical spectrums can be processed to derive experimental data related to the concentration and/or the solubility of asphaltenes of the hydrocarbon fluid sample.

In one embodiment, the processing of the stored optical spectrums involves:

calculating a plurality of characteristic optical densities that are associated with the solvent fractions for the filtered mixtures that result from iii) in each given iteration;

identifying a function that corresponds to a number of the plurality of characteristic optical densities; and calculating a parameter related to the solubility of asphaltenes of the hydrocarbon fluid sample based on a parameter of the function.

Each given one of the plurality of characteristic optical densities can be calculated by subtraction of an optical density component characteristic of the maltenes (diluted oil component) of the hydrocarbon fluid sample from an optical density component characteristic of the filtered mixture (permeate) that results from iii) in a given iteration. The optical density component characteristic of the maltenes can be derived from optical density measurements at a plurality of different wavelengths (e.g., at 600 nm and 800 nm), and the optical density component characteristic of the filtered mixture that results from iii) in a given iteration is derived from optical density measurements at a plurality of different wavelengths (e.g., at 600 nm and 800 nm).

The parameter related to the solubility of asphaltenes of the hydrocarbon fluid sample can be a critical solubility parameter $\delta_{cr}$ of the solvent at which asphaltenes will reach incipient flocculation or demixing. The critical solubility parameter $\delta_{cr}$ is empirically related to the asphaltene (or any other solute) solubility parameter $\delta_a$ by an equation of the form $$\delta_a = \delta_{cr} + 4 \text{ MPa}^{1/2}.$$

This equation assumes immiscibility of asphaltene and the solvent precipitant blend to occur at a solubility parameter difference of 4 MPa$^{1/2}$, a difference which may vary slightly as known from polymer sciences.

The experimental data related to the solubility of asphaltenes of the hydrocarbon fluid sample can be used to calibrate a model that describes the phase behavior of asphaltene-containing petroleum fluids. For example, the model can include at least one asphaltene solubility parameter, and the experimental data can be used to derive a value for the at least one asphaltene solubility parameter.

The experimental data related to the solubility of asphaltenes of the hydrocarbon fluid sample can also be used to derive at least one of a solubility blending number and an insolubility number for the hydrocarbon fluid sample. The solubility blending number and the insolubility number of the hydrocarbon fluid sample can be used as a criterion for oil compatibility of a mixture, wherein the criterion involves comparing the volume average solubility blending number of the components of the mixture and the insolubility number of any asphaltene-containing component of the mixture.

The solvent fluid used for the method can be selected from the group consisting of toluene, dichloromethane (DCM), xylenes, benzene, methyl naphthalene, cyclohexane, tetrahydrofuran (THF), chloroform, trichloroethylene, tetrachloroethylene, carbon tetrachloride, and any other fluids that dissolve asphaltenes. The precipitant fluid used for the method can be selected from the group consisting of n-heptane, n-hexane, n-pentane, petroleum ether, ethyl acetate, alcohols and any other fluids that precipitate asphaltenes.

DETAILED DESCRIPTION

Figure 1:
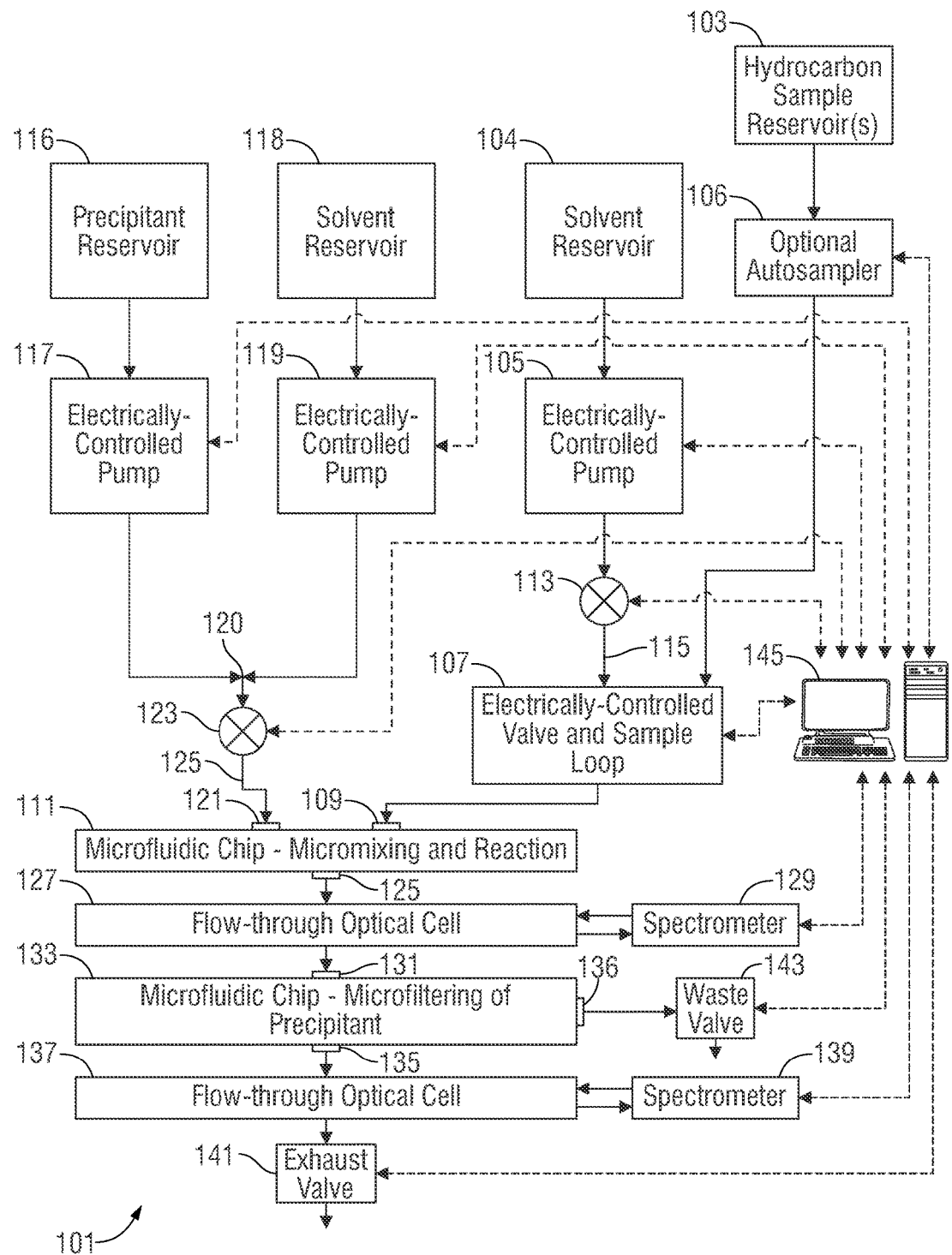
FIG. 1 is a block diagram of an automated test apparatus configured to analyze the solubility of asphaltenes of a hydrocarbon fluid sample in accordance with the present disclosure.

Illustrative embodiments of the disclosed subject matter of the application are described below. In the interest of clarity, not all features of an actual implementation are described in this specification. It will of course be appreciated that in the development of any such actual embodiment, numerous implementation-specific decisions must be made to achieve the developer's specific goals, such as compliance with system-related and business-related constraints, which will vary from one implementation to another. Moreover, it will be appreciated that such a development effort might be complex and time-consuming but would nevertheless be a routine undertaking for those of ordinary skill in the art having the benefit of this disclosure.

As used herein, the term "microfluidics" or "microfluidic" refers to a device, apparatus or system that deals with the behavior, precise control, and manipulation of fluids that are geometrically constrained to a small, typically sub-millimeter, scale. The device, apparatus, or system can employ small, typically sub-millimeter, scale channels that are etched into planar substrates, such as glass, where networks of these embedded channels transport the sample from one operation to the next. The manipulation of small volumes of fluid enables precise control of reagents and seamless automation of several consecutive steps.

The subject matter of the disclosure relates to the measurement of asphaltene solubility properties. The measurement of asphaltene solubility properties can be performed on stock tank oil with a series of titration experiments. The asphaltene molecule was defined using a solvent separation technique pioneered by Boussingault in 1837 and refined by Nellensteyn in the 1920's. Later research coupled solvent separation techniques with solution theory to describe asphaltene yield and stability, e.g., the Hildebrand solubility parameter as described in Mitchell, D. L. and Speight, J. G., "The solubility of asphaltenes in hydrocarbon solvents," *Fuel*, Vol. 52(2), 1973, pp. 149-152, and Hirschberg et al., "Influence of Temperature and Pressure On Asphaltene Flocculation," *Society of Petroleum Engineers Journal*, Vol. 24(3), 1984, pp. 283-293.

Since then, two mainstream measurement strategies have evolved to determine asphaltene solubility parameters, categorized as miscibility studies and precipitation schemes as described in Rogel, E., Ovalles, C. and Moir, M., "Asphaltene Stability in Crude Oils and Petroleum Materials by Solubility Profile Analysis," *Energy & Fuels*, Vol. 24(8), 2010, pp. 4369-4374. It is typical for both cases that asphaltenes are initially precipitated from the oil using solvent extraction and separated with filtration or centrifugation, as prescribed by standards such as ASTM D6560 as described below.

For the miscibility studies, the isolated solid asphaltenes are added to a pre-mixed and known ratio of solvent and precipitant as described in Mannistu, K. D., Yarranton, H. W. and Masliyah, J. H., "Solubility modeling of asphaltenes in organic solvents," *Energy & Fuels*, Vol. 11(3), 1997, pp. 615-620; Yarranton, H. W. and Masliyah, J. H., "Molar Mass Distribution and Solubility Modeling of Asphaltenes," *AIChE Journal*, Vol. 42(12), 1996, pp. 3533-3543; and Alboudwarej, H. et al., "Regular Solution Model for Asphaltene Precipitation from Bitumens and Solvents," *AIChE Journal*, Vol. 49(11), 2003, pp. 2948-2956. After sufficient time and mixing, the supernatant is removed and the mass of the undissolved asphaltene solids is measured. Alternatively, the mass of the dissolved asphaltenes can be measured gravimetrically after decanting and evaporating the excess solvent in the supernatant. An asphaltene solubility profile can be measured by discretely or continuously sweeping through an increasing gradient, from solvent to non-solvent combinations, with each mixture having a known and calculable solubility parameter. In this case, one is determining the fractional amount of asphaltene material that can be dissolved or solubilized in a variety of solvent combinations through subtraction of the undissolved mass from the starting mass.

In the precipitation schemes, the isolated asphaltenes are first dissolved in a solvent like toluene or dichloromethane and then titrated with known non-solvents to measure the fractional precipitation as described in Mannistu, K. D., Yarranton, H. W. and Masliyah, J. H., "Solubility modeling of asphaltenes in organic solvents," *Energy & Fuels*, Vol. 11(3), 1997, pp. 615-620; Spiecker, P. M., Gawrys, K. L. and Kilpatrick, P. K., "Aggregation and solubility behavior of asphaltenes and their subfractions," *Journal of Colloid and Interface Science*, Vol. 267(1), 2003, pp. 178-193; Yarranton, H. W. and Masliyah, J. H., "Molar Mass Distribution and Solubility Modeling of Asphaltenes," *AIChE Journal*, Vol. 42(12), 1996, pp. 3533-3543; and Wattana, P. et al., "Characterization of Polarity-Based Asphaltene Subfractions," *Energy & Fuels*, Vol. 19(1), 2005, pp. 101-110.

A typical experiment involves manual mixing of the dilute asphaltene solution with a known volume of precipitant, separating solid asphaltenes, monitoring the fractional precipitation (e.g. gravimetrically or optically), creating a profile and extracting solubility parameters. This assumes a constant solubility parameter difference between precipitant and precipitate in the range of 4 $MPa^{1/2}$ as known from polymer phase behavior as described in Hildebrand, J. H. and Scott, R. L., "The solubility of nonelectrolytes," Reinhold Publishing Corporation, 1950, and Andersen, S. I. and Speight, J. G., "Thermodynamic Models for Asphaltene Precipitation and Solubility," *Journal of Petroleum Science and Engineering* 53, 1999. Or the solubility parameter is obtained by calibrating a given model to the experimental data as described by Andersen, S. I. and Stenby, E. H., "Thermodynamics of asphaltene precipitation and dissolution investigation of temperature and solvent effects," *Fuel Science and Technology International* 14 (1-2), 1996, pp. 261-287. In miscibility and precipitation cases, the experimental effort necessary to determine asphaltene solubility parameters is not always practical or economical and it may even show apparent hysteresis effect depending the route taken as described in Andersen, S. I., "Hysteresis in precipitation and dissolution of petroleum asphaltenes," *Fuel Science and Technology International* 10 (10), 1993, pp. 1743-1749.

A solubility profile that is comprised of many discrete points requires several manual experiments, which can easily take days or weeks to complete. Further, these experiments tend to require knowledgeable staff and consume many liters of solvent and a substantial amount of crude oil. Alternative approaches and technology platforms have been proposed to reduce experimental bottlenecks.

U.S. Patent Application Publications US 2011/0062058 and US 2012/0160015 describe methods to evaluate solubility on high performance liquid chromatography equipment. In these methods, asphaltenes are precipitated using a solvent like n-heptane and retained by a column packed with an inert material, which acts like a filter. The mobile phase is gradually changed to a solvent that readily dissolves the asphaltenes and the output profile is monitored. The dissolved asphaltene concentration, or signal, versus time is evaluated to extract asphaltene solubility parameters as described in Rogel, E., Ovalles, C. and Moir, M., "Asphaltene Stability in Crude Oils and Petroleum Materials by Solubility Profile Analysis," *Energy & Fuels*, Vol. 24(8), 2010, pp. 4369-4374. The test can be completed in 35 minutes. One potential drawback of this approach is the variability of apparatus-to-apparatus performance. When this system generates solubility profiles, the redissolved asphaltenes undergo a varying degree of sample dispersion that arises from the fluid dynamics of the system. Achieving repeatable profile measurements from machine-to-machine may prove difficult due to differences in connectors, interfaces, and columns. For instance, it is well known that slight variations in column packing efficiency lead to notable differences in sample plug dispersion as mentioned in Knox, J. H. "Band Dispersion in Chromatography—A Universal Expression for the Contribution from the Mobile Zone," *Journal of Chromatography* A 960, no. 1-2 (2002): 7-18.

U.S. Patent Application Publication US 2004/0012782 describes a technique that employs laser illumination and measurement of light scattering to determine whether asphaltenes are soluble or insoluble in a solution of petroleum oil, a mixture of petroleum oils, derived oils, and mixtures or combinations of solvents. The technique claims the ability to measure insolubility number and solubility blending number, which are related to solubility parameters as described in Wiehe, I. A., "Asphaltene solubility and fluid compatibility," *Energy & Fuels*, Vol. 26(7), 2012, pp. 4004-4016. The technique also claims the ability to determine the onset of asphaltene aggregation and disaggregation in solution. The technique employs a measurement chamber described as a "thin cell" filled with oil mixture.

The process described by ASTM D6703—Standard Test Method for Automated Heithaus Titrimetry, semi-automates the measurement of the so called P-value or the asphaltene peptizability parameter and the maltene peptizing parameter. The standard is based on work by Heithaus, J. J., "Measurement and significance of asphaltene peptization," *American Chemical Society, Division of Petroleum Chemistry Preprints*, Vol. 5(4), 1960, pp. A-23-A-37, with similar variants published in the literature, such as Pauli, A. T., "Asphalt compatibility testing using the automated Heithaus titration test," *American Chemical Society, Division of Fuel Chemistry Preprints*, Vol. 41(4), 1996, pp. 1276-1280, and Andersen, S. I., "Flocculation onset titration of petroleum asphaltenes," *Energy & Fuels*, Vol. 13(2), 1999, pp. 315-322. U.S. Pat. No. 7,736,900 relates to this method and a device that practices this patent can be purchased from Koehler Instrument Company, Inc. of Bohemia, N.Y., USA. Note that filtration is absent in this design, there is minimal automation in the generation of solvent mixtures, and each data point uses the initial sample to be diluted in solvent, which is done manually. Mertens, E. W. *ASTM Bulletin.* 1960, 40 (TP 218) applied the Heithaus titration to generate critical solubility parameters of asphalt for the correlation of durability.

This disclosure presents a rapid and automated method for determining asphaltene solubility profiles and derived parameters that is based on optical absorbance and microfluidic technology.

FIG. 1 depicts an illustrative embodiment of an apparatus 101 for automated fluid analysis of a hydrocarbon sample. The apparatus 101 includes a reservoir 103 that holds a hydrocarbon sample and an optional autosampler 106 that is fluidly coupled between the reservoir 103 and an electrically-controlled valve and sample loop 107 with a defined volume. The hydrocarbon sample can include lighter (more volatile) molecular weight hydrocarbon components as well as heavy (less volatile) molecular weight components such as heavy oil and bitumen. The autosampler 106 and the sample loop 107 can be operated to inject a defined volumetric plug of the hydrocarbon sample held by the reservoir 103 into the defined volume of the sample loop 107. Alternatively, a defined volumetric plug of the hydrocarbon sample held by the reservoir 103 can be injected manually into the defined volume of the sample loop 107. The apparatus 101 also includes a reservoir 104 and an electrically-controlled pump 105 that is fluidly coupled to the reservoir 104. The reservoir 104 holds a fluid (referred to herein as a "solvent") that dissolves asphaltene solids when present in a hydrocarbon sample. The solvent can be toluene, dichloromethane (DCM), xylenes, benzene, methyl naphthalene, cyclohexane, tetrahydrofuran (THF), chloroform, trichloroethylene, tetrachloroethylene, carbon tetrachloride, carbon disulfide, and other suitable solvents. The reservoir 104 and the pump 105 are operated to move (or push) the defined volumetric plug of the hydrocarbon sample loaded into the sample loop 107 such that it flows (for example, at or near a desired flow rate) into an inlet 109 of a microfluidic chip 111. A pressure sensor 113 can be disposed within the flow line 115 between the pump 105 and the valve and sample loop 107 in order to monitor the pressure at the outlet of pump 105. Such pump pressure can be can be used as a form of feedback to adjust the operation of the pump 105 in order to maintain pressure levels within the pressure rating of the apparatus 101 and to ensure that the flow of the defined volumetric plug of the hydrocarbon sample into the inlet 109 occurs as desired. Thus, the pressure sensor 113 can be used as a form of feedback for the stability of the flow of the defined volumetric plug of the hydrocarbon sample into the inlet 109. The pump 105 can be an electrically-controlled syringe pump, such as the Mitos Duo XS-Pump sold commercially by The Dolomite Center Limited of Royston, UK, where the syringe of the pump acts as the reservoir 104 that stores the solvent.

The apparatus 101 also includes a reservoir 116 and an electrically-controlled pump 117 that is fluidly coupled to the reservoir 116. The reservoir 116 holds a fluid (referred to herein as a "precipitant") that causes asphaltenes to precipitate from a hydrocarbon sample when present. The precipitant can be an n-alkane (such as n-heptane ($C_7H_{16}$), n-hexane ($C_6H_{14}$), or n-pentane ($C_5H_{12}$)) or other solvents, such as petroleum ether, ethyl acetate, alcohols or any other solvent which can cause asphaltene precipitation due to a limited solubility. The apparatus 101 also includes a reservoir 118 and an electrically-controlled pump 119 that is fluidly coupled to the reservoir 118. The reservoir 118 holds a fluid (referred to herein as a "solvent") that dissolves asphaltene solids when present in a hydrocarbon sample. The solvent can be toluene, dichloromethane (DCM), xylene, benzene, methyl naphthalene, cyclohexane, tetrahydrofuran (THF), chloroform, trichloroethylene, tetrachloroethylene, carbon tetrachloride, carbon disulfide, or any other solvent that dissolves asphaltenes. The solvent of the reservoir 118 can be the same solvent as stored in the reservoir 104. It is also possible for the pumps 105 and 119 to be configured to pump solvent from a shared reservoir. The outputs of the pumps 117, 119 are merged together at T-section 120 that combines the output of the two pumps 117, 119. In an alternate configuration, a two-port microfluidic mixer chip can be used instead of the T-section 120 in order to combine the output of the two pumps 117, 119. The pumps 117, 119 are operated to inject the precipitant alone, the solvent alone, or a mixture of a controlled ratio of the precipitant and the solvent into inlet 121 of microfluidic chip 111. A pressure sensor 123 can be disposed within the flow line 125 between the T-section 120 and the inlet 121 in order to monitor the pump pressure of the pumps 117, 119. Such pump pressure can be used as a form of feedback to adjust the operation of the pumps 117, 119 in order to maintain pressure levels within the pressure rating of the apparatus 101 and to ensure that the flow of the precipitant alone, the solvent alone, or the controlled ratio of the precipitant and the solvent into the inlet 121 occurs as desired. Thus, the pressure sensor 123 can be used as a form of feedback for the stability of the flow into the inlet 121. The pressure sensor 123 can also be used to detect an overpressure of apparatus 101, such as may result from excessive asphaltene build up, so that the operation of the apparatus 101 can be halted. The pumps 117, 119 can be electrically-controlled syringe pumps, such as the Mitos Duo XS-Pump, where the syringe of the respective syringe pumps acts as the reservoirs 116, 118 that hold an amount of the precipitant and the solvent, respectively.

The microfluidic chip 111 includes an internal mixer section that provides microfluidic mixing of the fluids introduced into the inlets 121 and 109 and an internal reactor section that provides a microfluidic flow path that allows for microfluidic processes where solid asphaltene content (typically referred to as asphaltene floccules or asphaltene flocks) precipitate from the mixture generated by the mixer section. The asphaltene flock is carried as a suspension in the liquid phase content of the mixture. The liquid phase content of the mixture includes the maltenes of the hydrocarbon sample, which are the lower molecular weight components of the hydrocarbon sample that remain after removing the precipitated asphaltene content. The maltenes are soluble in the solvent-precipitant mixture. The microfluidic chip 111 also includes an outlet port 125 at the downstream end of the reactor section flow path.

The outlet port 125 of the microfluidic chip 111 is fluidly coupled to the inlet of a flow-through optical cell 127. A spectrometer 129 is optically coupled to the flow-through optical cell 127 and can be operated to derive an optical spectrum of the fluid mixture that flows from the outlet port 125 of the microfluidic chip 111 and through the flow-through optical cell 127.

The outlet of the flow-through optical cell 127 is fluidly coupled to an inlet port 131 of a microfluidic chip 133. The inlet port 131 is fluidly coupled to an internal filter section that provides microfluidic filtering that is configured to trap solid phase hydrocarbon components (i.e., the asphaltene flock) while passing soluble liquid phase hydrocarbon components (the permeate—which include the maltenes of the hydrocarbon sample) to an outlet port 135. The internal filter section of the microfluidic chip 133 is also fluidly coupled to a waste port 136 that allows for flushing and removal of the solid phase hydrocarbon components (i.e., the asphaltene flock) that is trapped by the internal filter section of the microfluidic chip 133 through an electrically-controlled waste valve 143.

The outlet port 135 of the microfluidic chip 133 is fluidly coupled to the inlet of a flow-through optical cell 137. A spectrometer 139 is optically coupled to the flow-through optical cell 137 and can be operated to derive an optical spectrum of the fluid that flows from the outlet port 135 of the microfluidic chip 133 and through the flow-through optical cell 137. An electrically-controlled exhaust valve 141 can be fluidly coupled to the outlet of the flow-through optical cell 137.

Figure 2:
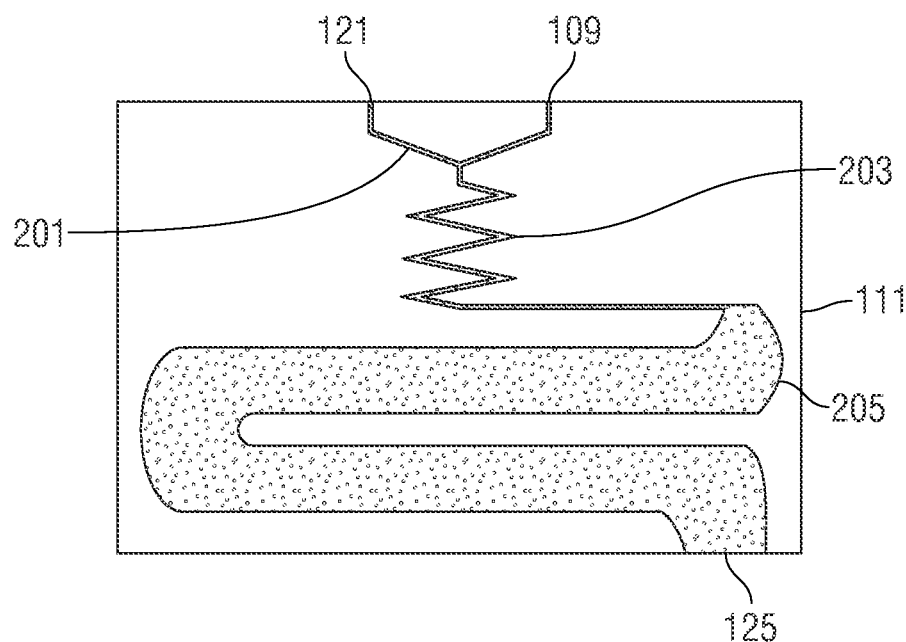
FIG. 2 is a schematic representation of one embodiment of the microfluidic chip 111 of FIG. 1.

FIG. 2 is a schematic view of one embodiment of the microfluidic chip 111 of FIG. 1, which includes two inlet ports 109 and 121 and a passive mixer section that is fluidly coupled to the two inlet ports 109, 121. The passive mixer section includes a y-type junction part 201 that leads from the two inlet ports 109, 121 to a mixing part 203. The passive mixer section (parts 201 and 203) provides microfluidic mixing of the fluids introduced into the inlet ports 109, 121. The mixing part 203 can employ chaotic split and recombine microfluidic mixing techniques or other suitable microfluidic techniques as described in Nam-Trung Nguyen and Zhigang Wu, "Micromixers—a Review," *Journal of Micromechanics and Microengineering* 15, no. 2 (2005): R1, herein incorporated by reference in its entirety. The downstream end of part 203 extends to a reactor part 205 that is realized by a serpentine path that has larger cross-sectional diameter as compared to the channel(s) of the mixing part 203 as is evident from FIG. 2. The reactor part 205 allows for precipitation of asphaltenes from the mixture generated by the passive mixer section. The asphaltene flock is carried as a suspension in the liquid phase content of the mixture. The downstream end of the larger diameter serpentine path of the reactor part 205 terminates at the outlet port 125. Note that the smaller dimensions of the mixing part 203 enable more effective and rapid mixing because of shorter diffusion distances and the larger dimensions of the reactor part 205 allow asphaltene flocculates to grow to a significant size for retention by the filter section 303 as described below.

Figure 3:
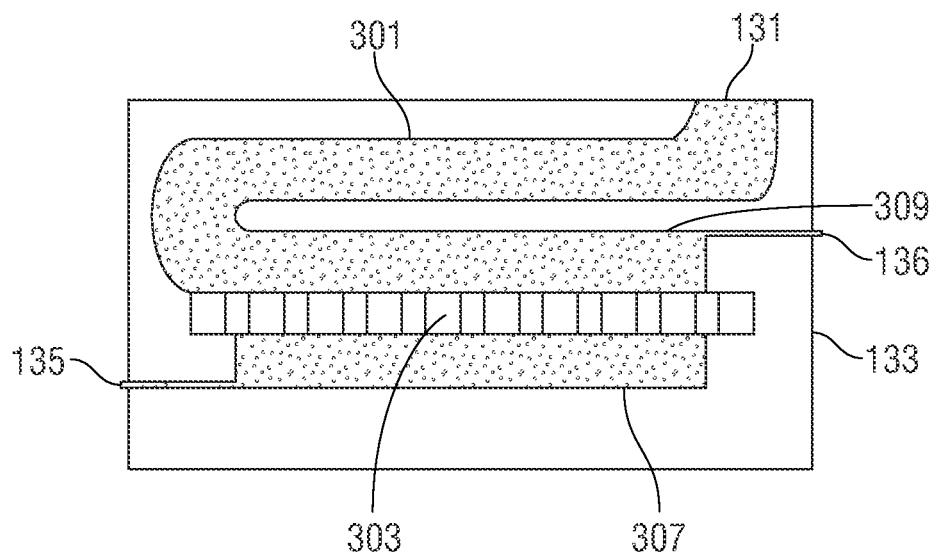
FIG. 3 is a schematic representation of one embodiment of the microfluidic chip 133 of FIG. 1.

FIG. 3 is a schematic view of one embodiment of the microfluidic chip 133 of FIG. 1, which includes an inlet port 131 and an inlet flow path 301 that leads to a filter section 303. The filter section 303 includes a membrane filter providing microfluidic filtering that is configured to trap solid phase hydrocarbon components (i.e., the asphaltene flock) while passing the permeate—the liquid phase hydrocarbon components which include the maltenes of the hydrocarbon sample—to an outlet flow path 307 (on its bottom side) that leads to the outlet port 135. The inlet of the membrane filter (disposed on its top side) includes a waste flow path 309 that leads to the waste port 136. The waste flow path 309 and the waste port 136 allow for flushing and removal of the solid phase hydrocarbon components (i.e., the asphaltene flock) that are trapped by the membrane filter of the filter section 303 of the microfluidic chip 133.

In one embodiment, the flow-through optical cells 127, 137 can be realized by an optical absorbance flow cell, such as the FIAlab SMA-Z-2.5 cell with fused silica windows and a 2.5 mm optical path and a 2.0 µl internal volume available from FIAlab Instruments, Inc. of Bellevue, Wash., USA. Custom flow cells that are either machined in the chip holders or integrated directly on the chip can also be used. The spectrometers 129, 139 can be realized by a broadband spectrometer, such as the model HR2000+ sold commercially by OceanOptics, Inc. of Dunedin, Fla., USA. The broadband spectrometer can be used in conjunction with a broadband light source which can be based on a tungsten filament bulb (such as the model LS-1 light source sold commercially by OceanOptics, Inc.). Fiber optic waveguides can be used to optically couple the optical absorbance flow cell to both the broadband light source and the broadband spectrometer.

A computer processing system 145 can be programmed with suitable control logic that interfaces to the electrically-controlled pumps 105, 117, 119 via wired or wireless signal paths therebetween, that interfaces to the electrically-controlled valves 107, 141, 143 via wired or wireless signal paths therebetween, and that interfaces to the pressure sensors 113, 123 via wired or wireless signal paths therebetween. The computer processing system 145 can also interface to the spectrometers 129, 139 via wired or wireless signal paths therebetween. The control logic of the computer processing system 145 (which can be embodied in software that is loaded from persistent memory and executed in the computing platform of the computer processing system 145) is configured to control the different parts of the apparatus 101 to carry out an automated sequence of operations (workflow) that characterizes the solubility profile of a hydrocarbon sample. The control logic can be configured by a testing script, which is input into and executed by the computer processing system 145 to perform automatic control operations as specified by the testing script. The computer processing system 145 can include a graphical user interface that allows the use to specify the sequence of automatic control operations and/or the parameters (such as pressures, flow rates, and temperatures) for such automatic control operations. An example of such an automated workflow is shown in FIGS. 4A and 4B.

Figure 4A:
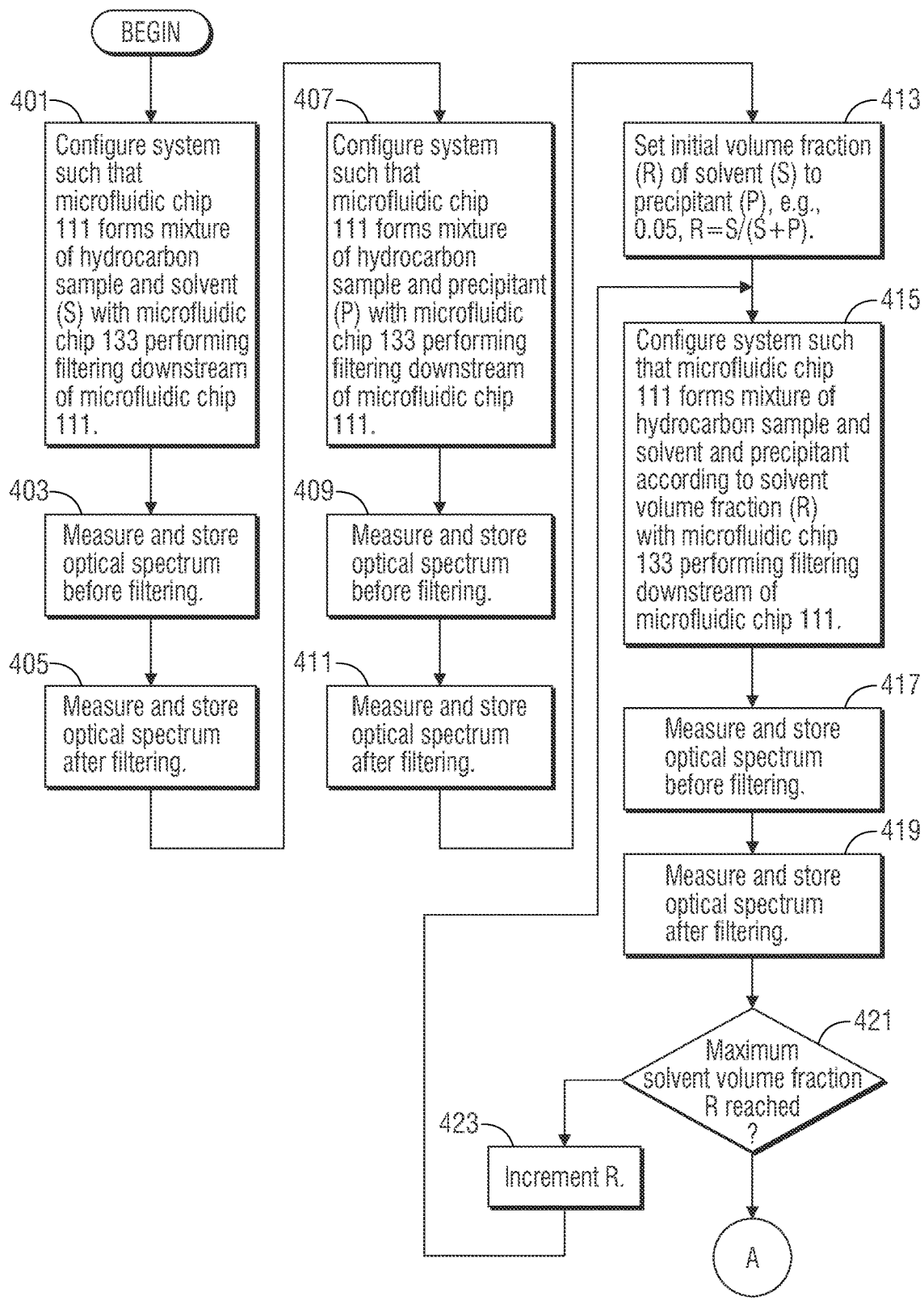
FIGS. 4A and 4B, collectively, are a flow chart of an automated workflow that employs the test apparatus of FIG. 1 to analyze the solubility of asphaltenes of a hydrocarbon fluid sample in accordance with the present disclosure.
Figure 4B:
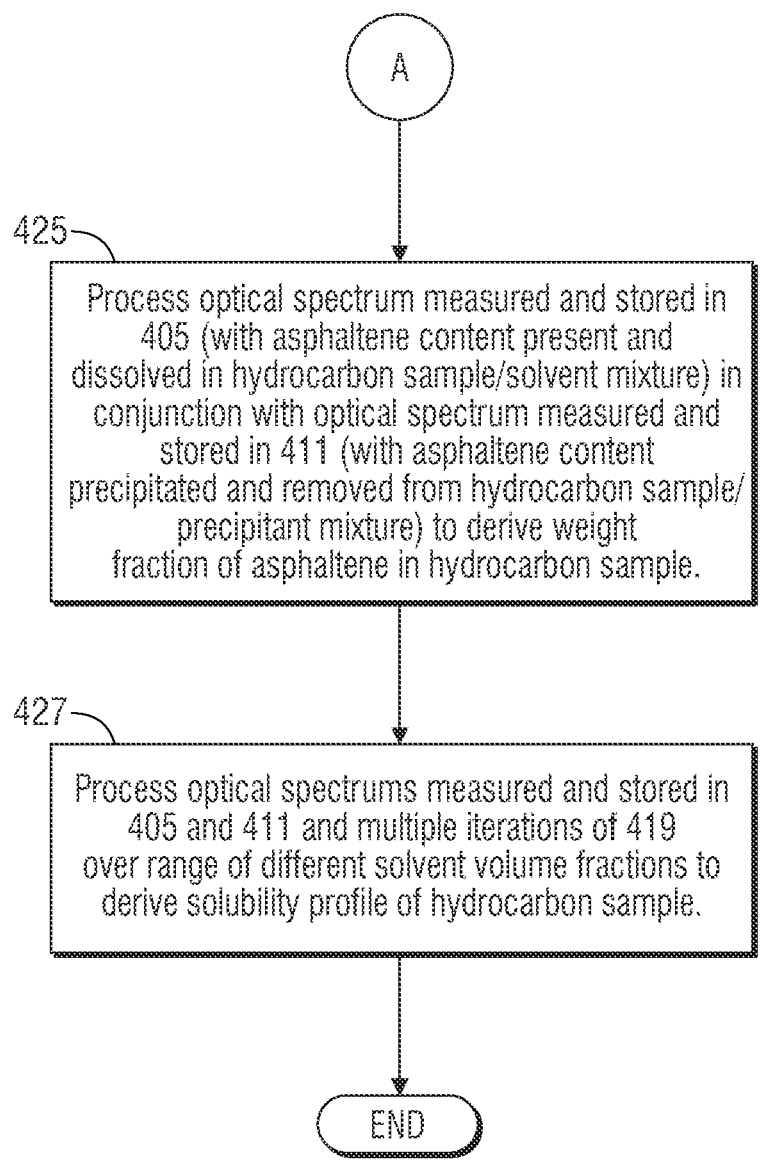

The workflow of FIGS. 4A and 4B assumes that the hydrocarbon sample is loaded into the reservoir 103 and the precipitant reservoir 116 and the solvent reservoirs 104, 118 are filled to desired levels with the precipitant (e.g., n-heptane) and the solvent (e.g., toluene or DCM), respectively.

The workflow begins at 401 where the autosampler 106 (if used), the pumps 105, 117, 119 and the valves 107, 141, 143 are controlled to inject the hydrocarbon sample into the inlet port 109 of the microfluidic chip 111 and to inject solvent alone from the reservoir 118 into the inlet port 121 of the microfluidic chip 111. The pumping rates for the two pumps 105, 119 are configured such that the mixing section of the microfluidic chip 111 forms a mixture where the hydrocarbon sample is diluted with a predetermined concentration of the solvent. The volume fraction of the solvent in the mixture can possibly be at or near 80:1 for heavy oil samples or possibly at or near 40:1 for black oil samples. In 401, the reactor section of the microfluidic chip 111 can allow the solvent of the sample/solvent mixture produced by the mixing section to dissolve most if not all of the asphaltene content of the sample/solvent mixture (if any asphaltene content is present from the hydrocarbon sample). The resultant sample/solvent mixture produced by the reactor section of the microfluidic chip 111 flows downstream to the outlet port 125 and then through the flow-through optical cell 127 to the inlet port 131 of the microfluidic chip 133 for filtering. The fluid that moves through the filter section of the microfluidic chip 133 (i.e., the "permeate") flows to the output port 135 of the microfluidic chip 133 and through the flow-through optical cell 137 to the exhaust valve 141.

In 403, the spectrometer 129 is configured to measure an optical spectrum of the sample/solvent mixture that flows through the corresponding flow-through optical cell 127 during 401. In this manner, the spectrometer 129 measures an optical spectrum of the sample/solvent mixture output from the microfluidic chip 111 before the mixture is filtered by the microfluidic chip 133. The computer processing system 145 is further configured to store the optical spectrum as measured in 403.

In 405, the spectrometer 139 is configured to measure an optical spectrum of the permeate that flows through the corresponding flow-through optical cell 137 during 401. In this manner, the spectrometer 139 measures an optical spectrum of the permeate that flows from the microfluidic chip 133. The computer processing system 145 is further configured to store the optical spectrum as measured in 405.

It is not expected that asphaltenes will be collected by the filtering section of the microfluidic chip 133 during the operation of 405. However, in the event that asphaltenes are collected by the filtering section of the microfluidic chip 133 during the operation of 405, a cleaning procedure can be executed to remove the collected asphaltenes before continuing to 407. This clean procedure can involve flowing solvent first across the membrane to waste via valve 143 and second a solvent flush of the system to the exhaust valve 141.

In 407, the autosampler 106 (if used), the pumps 105, 117, 119 and the valves 107, 141, 143 are controlled to inject the hydrocarbon sample into the inlet port 109 of the microfluidic chip 111 and to inject precipitant alone from the reservoir 116 into the inlet port 121 of the microfluidic chip 111. The pumping rates for the two pumps 105, 117 are configured such that the mixing section of the microfluidic chip 111 forms a mixture where the hydrocarbon sample is diluted with a predetermined concentration of the precipitant. The volume fraction of the precipitant in the mixture can possibly be at or near 40:1 for many hydrocarbon samples. In 407, the reactor section of the microfluidic chip 111 can allow the precipitant of the sample/precipitant mixture produced by the mixing section to precipitate out most if not all of the asphaltene content of the sample/precipitant mixture (if any asphaltene content is present from the hydrocarbon sample). The resultant sample/precipitant mixture (including the precipitated solid-form asphaltene content) that is produced by the reactor section of the microfluidic chip 111 flows downstream to the outlet port 125 and then through the flow-through optical cell 127 to the inlet port 131 of the microfluidic chip 133 for filtering. The filtering section of the microfluidic chip 133 traps the precipitated solid-form asphaltene content and allows the permeate (i.e., the liquid phase of the sample/precipitant mixture) to pass to the outlet port 135. The permeate flows from the outlet port 135 and through the flow-through optical cell 137 to the exhaust valve 141.

In 409, the spectrometer 129 is configured to measure an optical spectrum of the sample/precipitant mixture that flows through the corresponding flow-through optical cell 127 during 407. In this manner, the spectrometer 129 measures an optical spectrum of the sample/precipitant mixture output from the microfluidic chip 111 before the mixture is filtered by the microfluidic chip 133. The computer processing system 145 is further configured to store the optical spectrum as measured in 409.

In 411, the spectrometer 139 is configured to measure an optical spectrum of the permeate that flows through the corresponding flow-through optical cell 137 during 407. In this manner, the spectrometer 139 measures an optical spectrum of the permeate that flows from the microfluidic chip 133. The computer processing system 145 is further configured to store the optical spectrum as measured in 411.

It is expected that asphaltenes will be collected by the filtering section of the microfluidic chip 133 during the operation of 411. In this case, a cleaning procedure can be executed to remove the collected asphaltenes before continuing to 413-423. This clean procedure can involve flowing solvent first across the membrane to waste via valve 143 and second a solvent flush of the system to the exhaust valve 141.

In 413-423, the operations perform iterative operations over a range of values for a variable representing a solvent volume fraction (labeled "R"). The value of the solvent volume fraction R represents the relative volumetric ratio of the solvent (S) to the total volume (S+P) of the solvent and precipitant (P) in the combination of the solvent and the precipitant that is part of this mixture (i.e., R=S/(S+P) where S is the volume of the solvent and P is the volume of the precipitant). The iterative operations are performed over a range of values for the solvent volume fraction R that are incremented from an initial low value to a maximum threshold value.

In 413, the value of the solvent volume fraction R is set to an initial value, such as 0.05 or 5%.

In 415, the autosampler 106 (if used), the pumps 105, 117, 119 and the valves 107, 141, 143 are controlled to inject the hydrocarbon sample into the inlet port 109 of the microfluidic chip 111 and to inject both the precipitant from the reservoir 116 and the solvent from the reservoir 118 into the inlet port 121 of the microfluidic chip 111. The pumping rates for the three pumps 105, 117, 119 are configured such that the mixing section of the microfluidic chip 111 forms a mixture where the hydrocarbon sample is diluted with a combination of the solvent and the precipitant at the volumetric ratio corresponding to the solvent volume fraction R as initialized in 413. The concentration of the solvent/precipitant part of the mixture can also be defined by the pumping rates for the three pumps 105, 117, 119. In one example, the volume ratio of the solvent/precipitant part relative to the hydrocarbon sample part of the mixture is at or near 40 to 1. In 415, and dependent upon the relative concentration of the precipitant in the sample/solvent/precipitant mixture as dictated by the value of the solvent volume fraction R, the reactor section of the microfluidic chip 111 can allow the precipitant of the sample/solvent/precipitant mixture produced by the mixing section to precipitate out asphaltene content of the sample/solvent/precipitant mixture (if any asphaltene content is present from the hydrocarbon sample). The sample/solvent/precipitant mixture (including any precipitated solid-form asphaltene content) that is produced by the reactor section of the microfluidic chip 111 flows downstream to the outlet port 125 and then through the flow-through optical cell 127 to the inlet port 131 of the microfluidic chip 133 for filtering. The filtering section of the microfluidic chip 133 traps the precipitated solid-form asphaltene content (if any) and allows the permeate (i.e., the liquid phase of the sample/solvent/precipitant mixture) to pass to the outlet port 135. The permeate flows from the outlet port 135 and through the flow-through optical cell 137 to the exhaust valve 141.

In 417, the spectrometer 129 is configured to measure an optical spectrum of the sample/solvent/precipitant mixture that flows through the corresponding flow-through optical cell 127 during 415. In this manner, the spectrometer 129 measures an optical spectrum of the sample/solvent/precipitant mixture output from the microfluidic chip 111 before the mixture is filtered by the microfluidic chip 133.

In 419, the spectrometer 139 is configured to measure an optical spectrum of the permeate that flows through the corresponding flow-through optical cell 137 during 415. In this manner, the spectrometer 139 measures an optical spectrum of the permeate that flows from the microfluidic chip 133. The computer processing system 145 is further configured to store the optical spectrum as measured in 419.

In 421, the operations automatically determine whether a maximum threshold value for the solvent volume fraction R has been reached. If not, the operations continue to 423 where the value of the variable R is incremented and the operations continue to 415 to repeat the operations of 415 to 421 for the updated value of the variable R. If the maximum threshold value for the variable R has been reached, the operations continue to 425. In one example, the maximum threshold value for the variable R in 421 can be 0.95 or 95%, and 423 increments the value of the variable R by 0.05 or 5%. Thus, the iterative operations can extend over values of the solvent volume fraction R from 0.05 or 5% to 0.95 or 95% at increments of 0.05 or 5%.

FIGS. 5A, 5B, 5C, and 5D are schematic illustrations of the operations of 401-421.

Figure 5A:
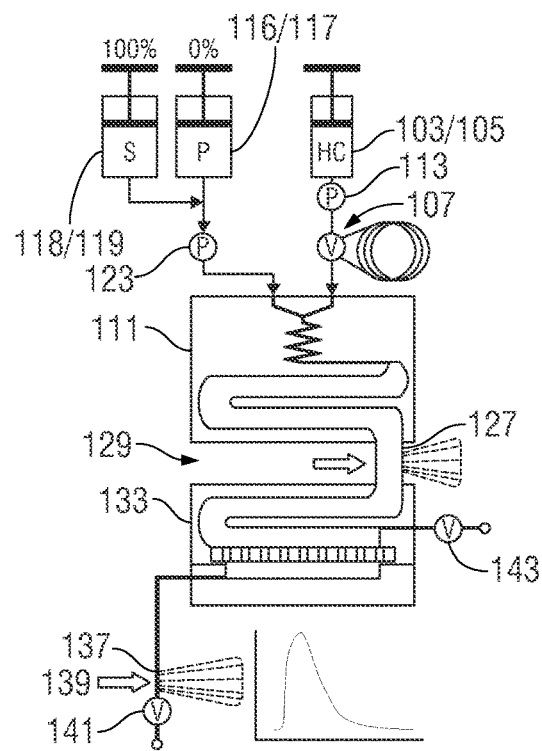
FIGS. 5A, 5B, 5C, and 5D are graphical illustrations of the operations carried out during various parts of the automated workflow of FIGS. 4A and 4B.

FIG. 5A illustrates the operations of 401 to 405 where the mixing section of the microfluidic chip 111 forms a mixture where the hydrocarbon sample is diluted with the solvent alone. The reactor section of the microfluidic chip 111 can allow the solvent of the hydrocarbon sample/solvent mixture to dissolve most if not all of the asphaltene content of the sample/solvent mixture (if any asphaltene content is present from the hydrocarbon sample). A graphical depiction of an optical spectrum of the mixture after filtering as measured by the spectrometer 139 is also shown.

Figure 5B:
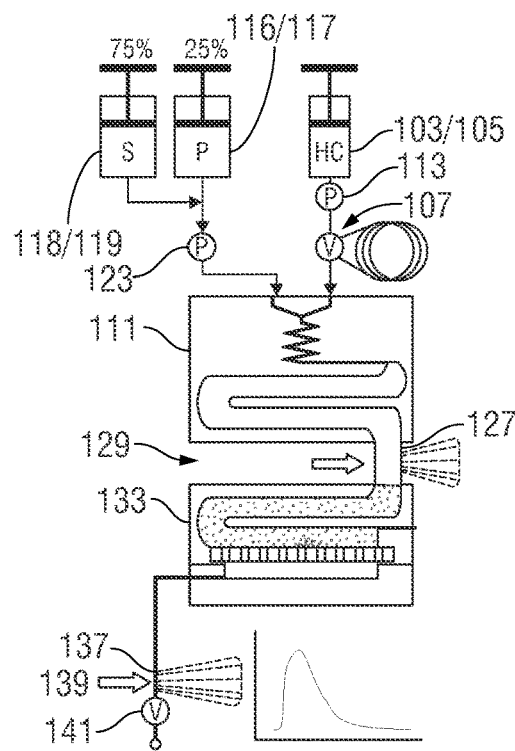
Figure 5C:
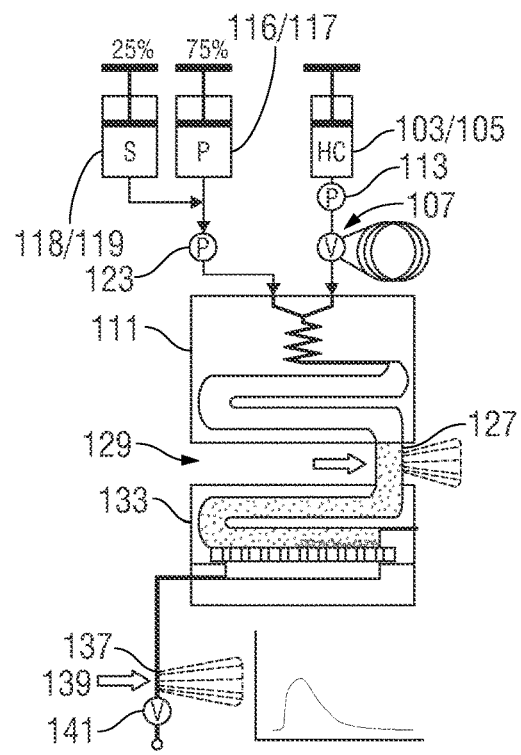
Figure 5D:
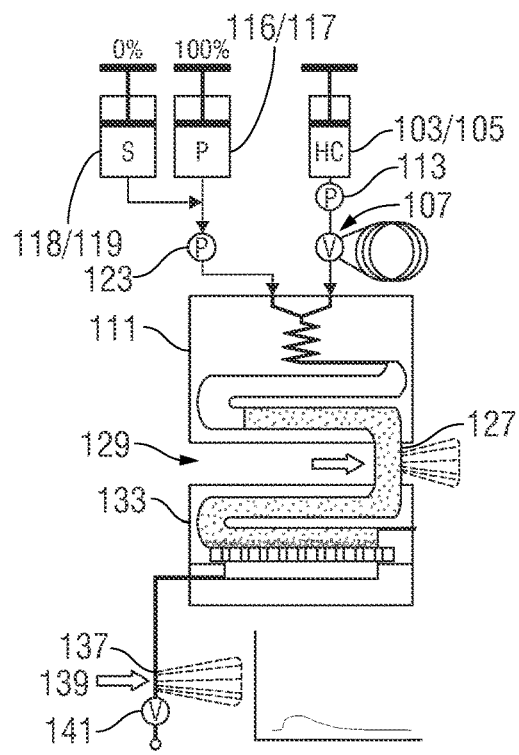

FIG. 5D illustrates the operations of 407 to 411 where the mixing section of the microfluidic chip 111 forms a mixture where the hydrocarbon sample is diluted with the precipitant alone. The reactor section of the microfluidic chip 111 can allow the precipitant of the sample/precipitant mixture to precipitate most if not all of the asphaltene content of the sample/precipitant mixture (if any asphaltene content is present from the hydrocarbon sample). A graphical depiction of an optical spectrum of the mixture after filtering as measured by the spectrometer 139 is also shown.

FIGS. 5B and 5C illustrate the operations of the 413 to 423 for two values of the solvent volume fraction R. In these operations, the mixing section of the microfluidic chip 111 forms a mixture where the hydrocarbon sample is diluted with a combination of the solvent and precipitant over a range of values for the solvent volume fraction R. The reactor section of the microfluidic chip 111 can allow the precipitant of the sample/precipitant mixture to precipitate asphaltene content of the sample/precipitant mixture (if any asphaltene content is present from the hydrocarbon sample) where the amount of precipitation is dependent upon the concentration of the precipitant in the mixture. A graphical depiction of an optical spectrum of the mixture after filtering as measured by the spectrometer 139 is also shown. FIG. 5B corresponds to the case where the solvent volume fraction R is 0.75 or 75%, and FIG. 5C corresponds to the case where the solvent volume fraction R is 0.25 or 25%.

Note that the optical density or absorbance of the optical spectrum is at a relative maximum (or darkest in color) for the case of FIG. 5A since most of the asphaltene content of the hydrocarbon sample is soluble and dissolved by the solvent, with very little precipitation of asphaltene content as well as very little filtration being performed by the microfluidic chip 133. The optical density or differential spectral absorbance of the optical spectrum is at a relative minimum (or lightest in color) for the case of FIG. 5D since most of the asphaltene content of the hydrocarbon sample is precipitated and removed by the filtration performed by the microfluidic chip 133. The optical density or differential spectral absorbance of the optical spectrums of the middle diagrams of FIGS. 5B and 5C fall between those of FIGS. 5A and 5D due to the partial asphaltene precipitation that arises from the corresponding values of the solvent volume fraction R and subsequent filtering performed by the microfluidic chip 133 that removes the precipitated asphaltene content.

In 425, the computer processing system 145 processes the optical spectrum measured and stored in 405 (with the asphaltene content present and dissolved in the hydrocarbon sample/solvent mixture) in conjunction with the optical spectrum measured and stored in step 411 (with the asphaltene content precipitated and removed from the hydrocarbon sample/precipitant mixture) in order to derive the weight fraction of asphaltene in the hydrocarbon sample. In one example, the processing of 425 can involve deriving a characteristic optical density (OD) or differential spectral absorbance (in absorbance units AU) of the asphaltene content of the hydrocarbon sample by the following equation:

$$\text{Differential Spectral Absorbance (AU)} = (OD@600\ nm_{Spectrum\ of\ 405} - OD@800\ nm_{Spectrum\ of\ 405}) - (OD@600\ nm_{Spectrum\ of\ 411} - OD@800\ nm_{Spectrum\ of\ 411}). \quad (1)$$

The first term of Eq. (1) is derived from the optical spectrum of 405 and represents the contribution of both asphaltene content and the maltenes to differential spectral absorbance. The second term of Eq. (1) is derived from the optical spectrum of 411 and represents the contribution of the maltenes alone to differential spectral absorbance. The subtraction of the optical density (OD) at 800 nm in both the first and second terms is meant to reduce the error from spectral offset introduced by light scattering and from other errors in the measurements. The characteristic optical density or differential spectral absorbance of the asphaltene content as derived from Eq. (1) can be correlated to a weight ratio of asphaltene content in the hydrocarbon sample based upon calibration data. Such calibration data can define the relationship of the characteristic optical density of the asphaltene content to asphaltene content measurements in hydrocarbon samples measured using some other technique (such as a conventional gravimetric technique, in which a series of hydrocarbon samples are collected and tested). A correlation factor can be applied to convert the characteristic optical density of the asphaltene content to a weight ratio of asphaltene content in the hydrocarbon sample as described in Schneider, M. H., Sieben, V. J., Kharrat, A. M., and Mostowfi, F., "Measurement of Asphaltenes Using Optical Spectroscopy on a Microfluidic Platform," *Analytical Chemistry* 85, no. 10 (2013): 5153-60, doi:10.1021/ac400495x, herein incorporated by reference in its entirety.

In 427, the computer processing system 145 processes the optical spectrums measured and stored in 405 and 411 and the multiple iterations of 419 over the range of different solvent volume fractions R in order to characterize the solubility of the asphaltene content of the hydrocarbon sample. In one example, the processing of 427 can involve deriving a characteristic optical density or differential spectral absorbance of the asphaltene content of the hydrocarbon sample over a range of different values for the solvent volume fraction R. For this analysis, the optical spectrum of 405 corresponds to the case where the solvent volume fraction R is 1 or 100% (i.e., only solvent and hydrocarbon sample), and the optical spectrum of 411 corresponds to the case where the solvent volume fraction R is zero or 0% (i.e., only precipitant and hydrocarbon sample).

For the case where the solvent volume fraction R is 0, the characteristic optical density $OD_{R=0}$ of the asphaltene content of the hydrocarbon sample can be derived by the following equation:

$$OD_{R=0} = (OD@600\ nm_{Spectrum\ of\ 405} - OD@800\ nm_{Spectrum\ of\ 405}) - (OD@600\ nm_{Spectrum\ of\ 411} - OD@800\ nm_{Spectrum\ of\ 411}). \quad (2)$$

This Eq. (2) is identical to Eq. (1) as described above. For the case where the solvent volume fraction R is 0.05, the characteristic optical density $OD_{R=0.05}$ of the asphaltene content of the hydrocarbon sample can be derived by the following equation:

$$OD_{R=0.05} = (OD@600\ nm_{Spectrum\ of\ 405} - OD@800\ nm_{Spectrum\ of\ 405}) - (OD@600\ nm_{Spectrum\ of\ 419\ where\ R=0.05} - OD@800\ nm_{Spectrum\ of\ 419\ where\ R=0.05}). \quad (3)$$

For the case where the solvent volume fraction R is 0.10, the characteristic optical density $OD_{R=0.10}$ of the asphaltene content of the hydrocarbon sample can be derived by the following equation:

$$OD_{R=0.10} = (OD@600\ nm_{Spectrum\ of\ 405} - OD@800\ nm_{Spectrum\ of\ 405}) - (OD@600\ nm_{Spectrum\ of\ 419\ where\ R=0.10} - OD@800\ nm_{Spectrum\ of\ 419\ where\ R=0.10}). \quad (4)$$

Similar equations can be used to derive $OD_{R=0.15}$ to $OD_{R=0.95}$ using the optical spectrum of 419 for the corresponding iteration of the solvent volume fraction R. For the case where the solvent volume fraction R is 1 or 100% (i.e., only solvent and hydrocarbon), the characteristic optical density $OD_{R=1}$ of the asphaltene content of the hydrocarbon sample can be derived by the following equation:

$$OD_{R=1} = (OD@600\ nm_{Spectrum\ of\ 405} - OD@800\ nm_{Spectrum\ of\ 405}). \quad (5)$$

Figure 6:
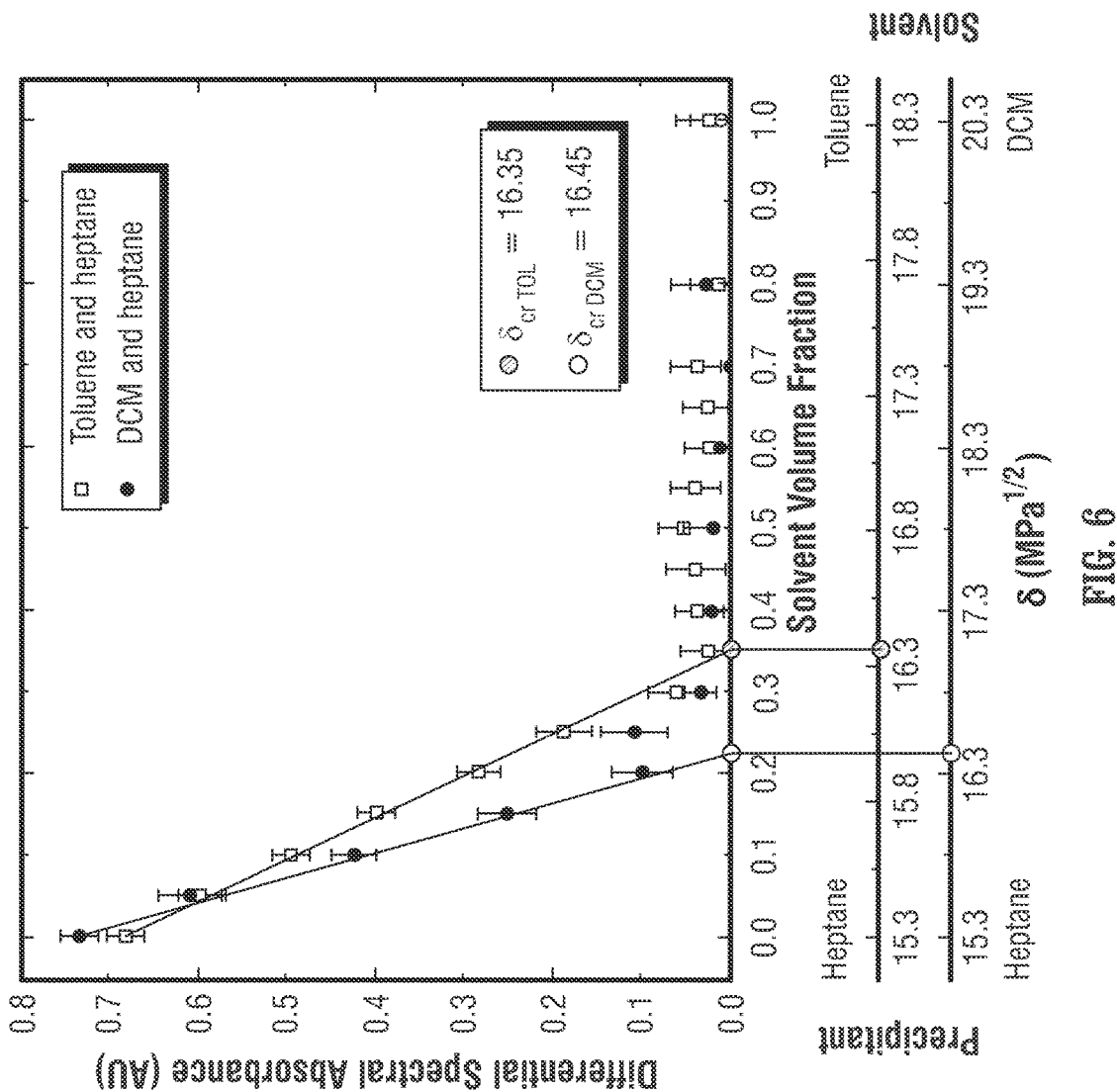
FIG. 6 is a graph of characteristic asphaltene differential spectral absorbance values as a function of solvent volume fraction as well as corresponding asphaltene solubility parameters that are derived from the automated workflow of FIGS. 4A and 4B.

The $OD_R$ values can be plotted as function of the solvent volume fraction R as shown in FIG. 6 in order to present in a graphical form the solubility profile of the hydrocarbon sample. Note that the first terms of Eqs. (2)-(5) are derived from the spectrum of 405 and represent the contribution of both asphaltene content and the maltenes to the $OD_R$ values. The second term of Eq. (2) is derived from the spectrum of 411 and represents the contribution of the maltenes alone to the $OD_R$ values. The second term of Eqs. (3)-(4) is derived from the spectrum of 419 and represents the contribution of the maltenes plus any soluble asphaltene molecules in the selected solvent-precipitant mixture. At low values of the solvent volume fraction R, only highly soluble asphaltenes dissolve and pass through with the maltenes. At high values of the solvent volume fraction R, the optical density of the maltenes plus dissolved asphaltenes approaches that of hydrocarbon diluted in solvent as most asphaltenes are soluble and pass through the filter membrane. The subtraction of the optical density (OD) at 800 nm in both the first and second terms is meant to reduce the error from spectral offset introduced by light scattering and from other errors in the measurements.

The analysis of 427 can also include deriving the solvent volume fraction $R_{fo}$ for asphaltene flocculation onset by fitting the $OD_R$ values over a predetermined limited range of R (such as from R=0 to R=0.4) to a function, such as a line or polynomial curve or other suitable function. For example, FIG. 6 illustrates the derivation of the solvent volume fraction $R_{fo}$ for asphaltene flocculation onset by fitting the $OD_R$ values over a predetermined limited range of R (such as from R=0 to R=0.4) to a best-fit line. The x-intercept of the fitted line yields the solvent volume fraction $R_{fo}$ for asphaltene flocculation onset for the hydrocarbon sample.

Note that FIG. 6 shows the analysis for experiments that utilize two different solvents, toluene for one case and DCM for the second case. For the experiment that utilized toluene as the solvent, the data points are empty squares and the fitted line crosses the x-intercept near R of 0.35. For the experiment that utilized DCM as the solvent, the data points are filled circles and the fitted line crosses the x-intercept near R of 0.23.

The solvent volume fraction $R_{fo}$ for asphaltene flocculation onset can be used to determine the critical Hildebrand solubility parameter of the asphaltenes in the hydrocarbon sample. If an assumption is made that asphaltenes begin to precipitate at a critical solvent-precipitant-hydrocarbon mixture composition, then the asphaltene Hildebrand solubility parameter $\delta_a$ can be estimated as:

$$\delta_a = \delta_{cr} + 4 \text{ MPa}^{1/2}. \qquad (6)$$

In this case, the critical solubility parameter $\delta_{cr}$ can be derived by correlation to the solvent volume fraction $R_{fo}$ or asphaltene flocculation onset (as dictated by the x-intercept of the best-fit line) as shown in FIG. 6. Specifically, the critical solubility parameter can be determined, when the hydrocarbon-solvent-precipitant mixture is dilute in terms of the hydrocarbon content, from the solvent volume fraction $R_{fo}$ for asphaltene flocculation onset as:

$$\delta_{cr} = R_{fo} * (\delta_s - \delta_p) + \delta_p \qquad (7)$$

where $R_{fo}$ is the solvent volume fraction for asphaltene flocculation onset, $\delta_s$ is the solubility parameter for the solvent (which can be set to 18.3 MPa$^{1/2}$ for the case where the solvent is toluene or can be set to 20.3 MPa$^{1/2}$ where the solvent is DCM), and $\delta_p$ is the solubility parameter of the precipitant (which can be set to 15.3 MPa$^{1/2}$ for the case where the precipitant is heptane).

If the hydrocarbon solubility parameter is estimated from, for example, refractive index correlations this may be included when substantial hydrocarbon is present in the solution using the normal volumetric mixing rule for solubility parameters of blends.

The bottom part of FIG. 6 shows two line graphs that represent the correlation function between the solvent volume fraction $R_{fo}$ for asphaltene flocculation onset and the critical solubility parameter $\delta_{cr}$ for two different cases. The upper line graph shows the correlation function between the solvent volume fraction $R_{fo}$ for asphaltene flocculation onset and the critical solubility parameter $\delta_{cr}$ for the case where toluene is used as the solvent and n-heptane is used as the precipitant. In this case, the solvent volume fraction $R_{fo}$ for asphaltene flocculation onset near 0.35 correlates to the critical solubility parameter $\delta_{cr\_TOL}$ of 16.35 MPa$^{1/2}$. The lower line graph shows the correlation function between the solvent volume fraction $R_{fo}$ for asphaltene flocculation onset and the critical solubility parameter $\delta_{cr}$ for the case where DCM is used as the solvent and n-heptane is used as the precipitant. In this case, the solvent volume fraction $R_{fo}$ for asphaltene flocculation onset near 0.23 correlates to the critical solubility parameter $\delta_{cr\_DCM}$ of 16.45 MPa$^{1/2}$. Thus, the measurements for both cases reveal a similar Hildebrand solubility parameter $\delta_a$ of 20.4 MPa$^{1/2}$ per Eq. (6). This value is consistent with the range of values 19-22 MPa$^{1/2}$ as reported in Andersen, S. I. and Speight, J. G., "Thermodynamic Models for Asphaltene Precipitation and Solubility," *Journal of Petroleum Science and Engineering* 53, 1999.

Note that the optical spectrums measured as part of 403 and 409 may not be necessary for the measurement. They are primarily used as a form of quality control. Specifically, these optical spectrums can be used to confirm that filtration was successful by noting the coloration changes before and after filtration. The pre-filter spectrum shows high absorbance and when asphaltenes precipitate there are large deviations to the average signal. This is caused by the flocks scattering incident light and appearing as large absorbance spikes. The filtered signal should be free of large variations and display a stable plateau of lower absorbance value.

Figure 7:
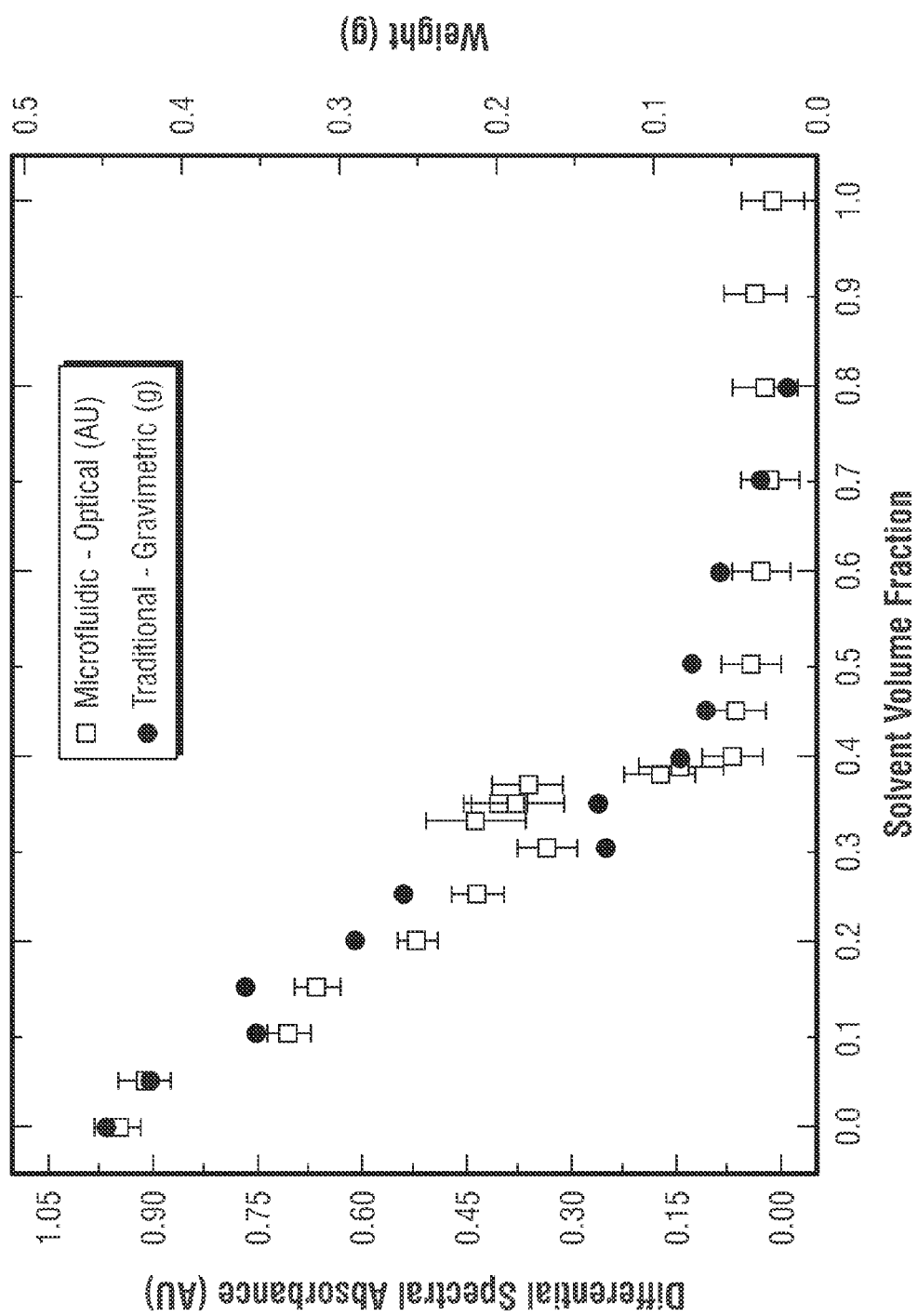
FIG. 7 is a graph of characteristic asphaltene differential spectral absorbance values (shown on the left vertical axis) as a function of solvent volume fraction (shown on the horizontal axis) as derived from an automated workflow similar to the workflow of FIGS. 4A and 4B for a hydrocarbon as well as the weight values of precipitated asphaltene content (shown on the right vertical axis) as a function of solvent fraction as derived from traditional gravimetric analysis of the same hydrocarbon.

FIG. 7 shows a profile of the optical density or differential spectral absorbance of a solvent-precipitant-hydrocarbon sample mixture over a range of values for the solvent volume fraction R as measured by an automated workflow employing microfluidic mixing, reacting, and filtering. FIG. 7 also shows the mass of precipitated asphaltenes from like solvent-precipitant-hydrocarbon sample mixtures over the same range of values for the solvent volume fraction R as measured by gravimetric analysis. The square data points are measurements of optical density plotted using the left vertical axis and the horizontal axis representing the range of values for the solvent volume fraction R. These data points were measured by an automated workflow employing microfluidic mixing, reacting, and filtering. The circular data points are measurements of the mass of precipitated asphaltenes from like solvent-precipitant-hydrocarbon sample mixtures over the same range of values for the solvent volume fraction R as measured by gravimetric analysis. The data shows similar linear and plateau trends between the two methods within the experimental error of the techniques. Similar to the plots of FIG. 6, one value of the solvent volume fraction $R_{fo}$ for asphaltene flocculation onset can be given by the x-intercept of the best-fit line of the differential spectral absorbance data points (the square data points) over a predetermined limited range of R (such as from R=0 to R=0.4). In this case, this x-intercept yields a value of the solvent volume fraction $R_{fo}$ for asphaltene flocculation onset of 0.499. Another value of the solvent volume fraction $R_{fo}$ for asphaltene flocculation onset can be given by the x-intercept of the best-fit line of the mass data points (the circular data points) over a predetermined limited range of R (such as from R=0 to R=0.4). In this case, this x-intercept yields a value of solvent volume fraction $R_{fo}$ for asphaltene flocculation onset of 0.490. Thus, the two methods report the flocculation point within a solvent volume fraction $R_{fo}$ of one percent.

Figure 8:
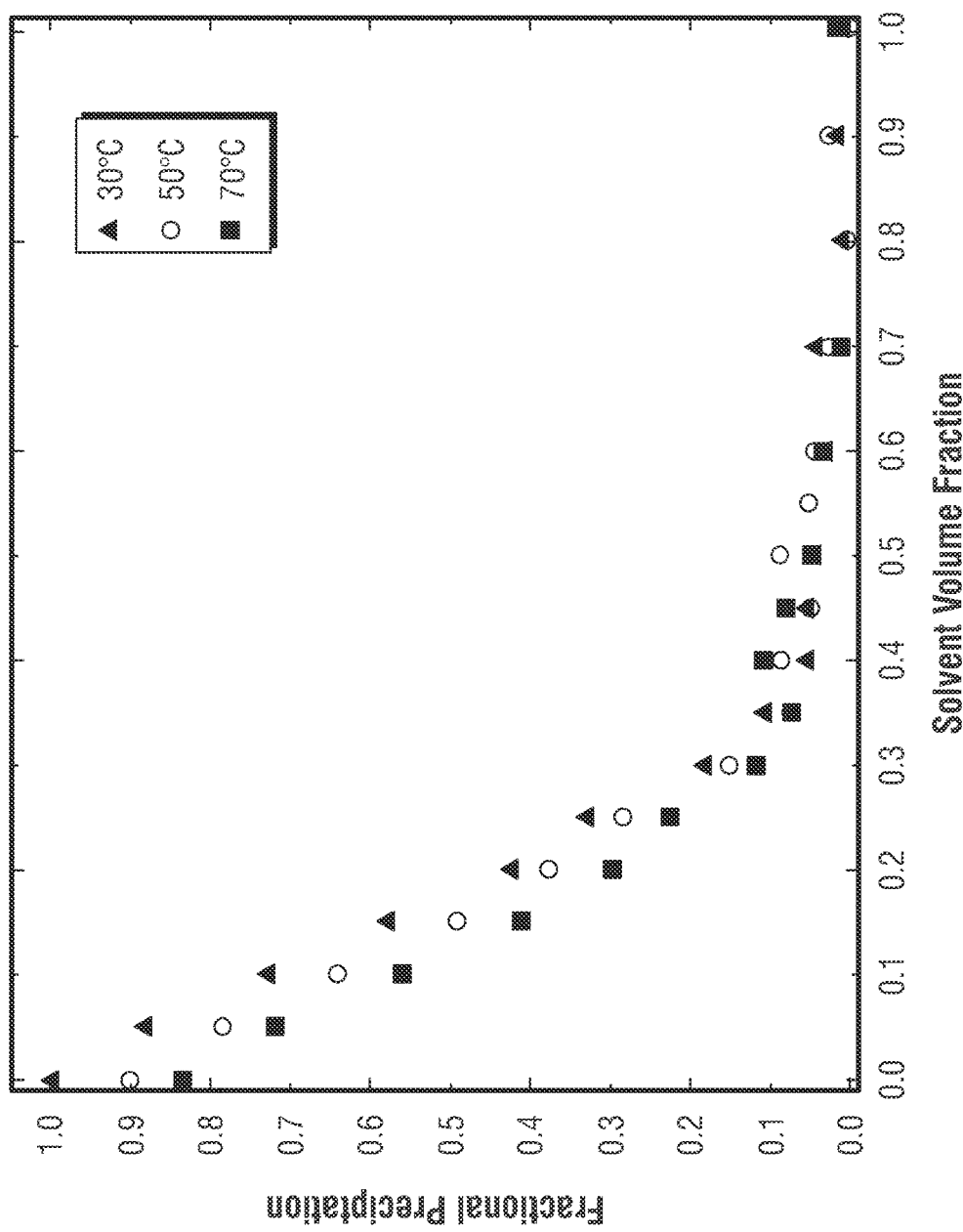
FIG. 8 is a graph of fractional asphaltene precipitation as a function of solvent volume fraction as derived from the automated workflow of FIGS. 4A and 4B over a number of different controlled system temperatures.

The solubility of the asphaltene content of the hydrocarbon sample is dependent on temperature. The temperature of the apparatus can be controlled during the workflow carried out by the apparatus 101 of FIG. 1 and repeated at different temperature settings. FIG. 8 shows the relative amount of fractional precipitation of asphaltenes over the range of solvent volume fractions R during the workflow of FIG. 4 with the temperature of the apparatus 101 controlled at three different temperatures (30° C., 50° C. and 70° C.) for the entire workflow. The data points are normalized relative to the maximum value of fractional precipitation of asphaltenes with the solvent volume fraction R of 0 for the 30° C. case. The data shows a trend as expected with the asphaltene solubility increasing (hence less fractional precipitation of asphaltenes) with an increase in temperature in agreement with the literature.

In an alternate embodiment, the hydrocarbon reservoir 103 and the electrically-controlled pump 105 can hold and dispense a hydrocarbon fluid sample derived by blending quantities of different hydrocarbons or by adding one or more additives to the hydrocarbons. The additives can be a diluent, a dispersant, an inhibitor, or other suitable additive. In this case, the workflow can be used to characterize the asphaltene solubility profile of the hydrocarbon fluid sample or a resulting blend. This analysis can be useful for identifying an appropriate additive that mitigates the problems that can arise from asphaltene precipitation of the particular hydrocarbon during its production and/or transport.

In another alternative embodiment, the method as described herein can be repeated over multiple iterations where the volume fraction of the hydrocarbon-containing sample relative to the precipitant and/or solvent is varied over the multiple iterations.

Figure 9:
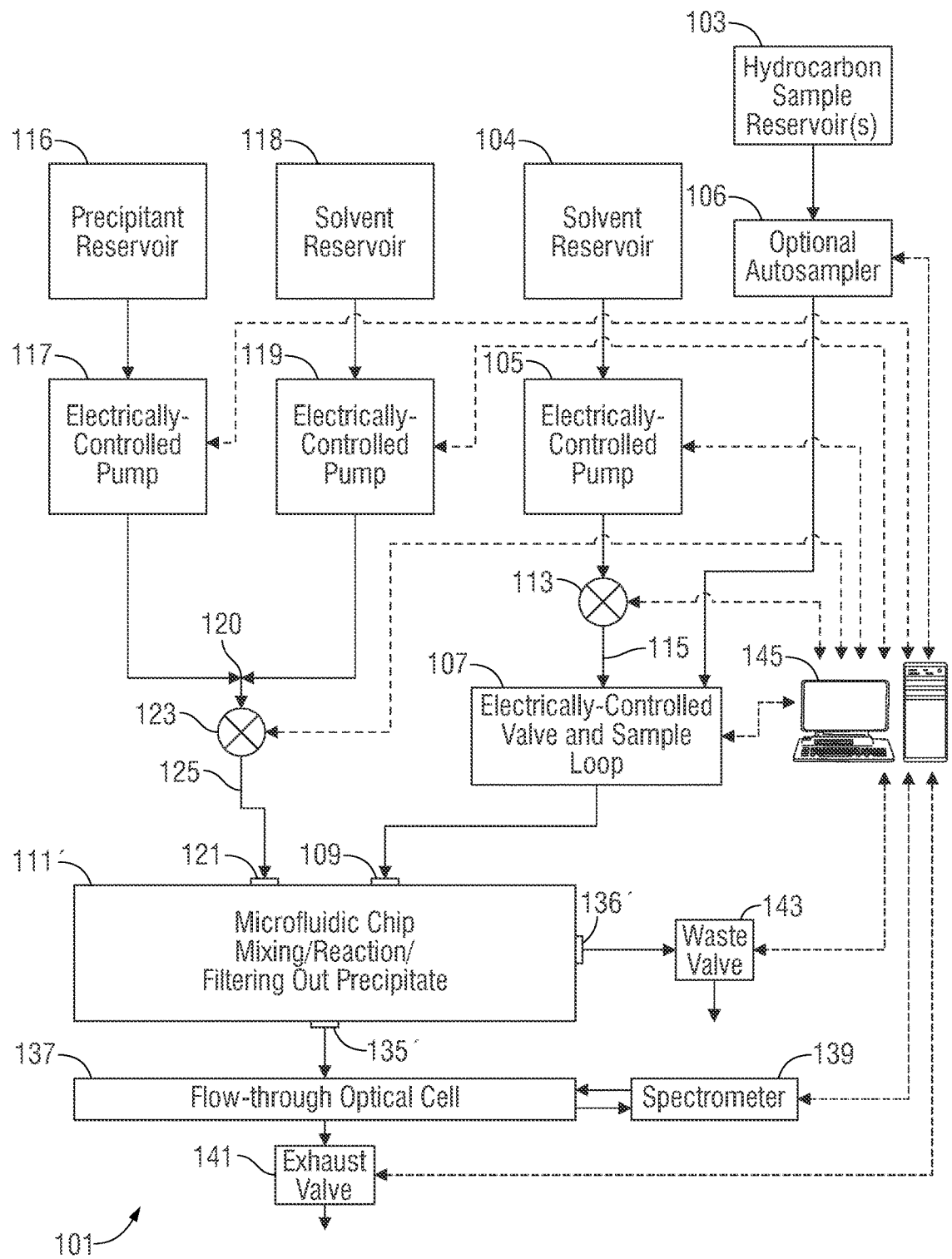
FIG. 9 is a block diagram of an alternate embodiment of an automated test apparatus configured to analyze the solubility of asphaltenes of a hydrocarbon fluid sample in accordance with the present disclosure.

FIG. 9 shows an apparatus 101' for automated fluid analysis of a hydrocarbon sample similar to the apparatus 101 of FIG. 1, where the flow-through optical cell 127 and spectrometer 129 of FIG. 1 are omitted and the functions of the two microfluidic chips 111, 133 of FIG. 1 are merged into one microfluidic chip 111' as shown.

The automated microfluidic testing apparatus and method of operation can provide the ability to rapidly measure asphaltene solubility parameters. The apparatus can be utilized with a variety of solvent/precipitant combinations and over multiple temperature ranges, which permits frequent and more accurate acquisition of asphaltene solubility parameters. The automated microfluidic testing apparatus can require minimal human intervention and can significantly reduce the testing time as well as the amount of reagent used for testing as compared to conventional approaches. Moreover, the reduction in measurement time can enable more frequent characterizations of hydrocarbon samples with blends, diluents, dispersants, inhibitors, and/or other suitable additives used in hydrocarbon fluid samples.

It is also contemplated that the solubility testing method and apparatus as described herein can be used to derive experimental data that is used to calibrate a model that describes the phase behavior of asphaltene-containing petroleum fluids. The model can be used to perform calculations with variations in either solvent or precipitant. As asphaltenes generally belong to a group of unknown components, the experimental data can be used to correlate or calibrate the model for engineering predictions or estimations.

In one example, Hirschberg et al, developed a simple model for asphaltene solubility in either oil or solvent based on the Flory-Huggins solution theory for polymer solubility as:

$$\ln \Phi_a = -1 + \frac{v_a}{v_m} - \frac{v_a}{RT}(\delta_a - \delta_m)^2 \quad (8)$$

where $\Phi_a$ is the volume fraction of asphaltene soluble in the mixture,
$v_a$ is the molar volume of asphaltene,
$v_m$ is the molar volume of the mixture,
$\delta_a$ is the solubility parameter of asphaltenes,
$\delta_m$ is the solubility parameter of the mixture,
T is the absolute temperature,
R is the universal gas constant.

The model of Eq. (8) assumes that a single pure solid asphaltene phase precipitates or is in equilibrium with the solution, and the molar solubility of the asphaltene is so small that this is almost equal to the soluble volume fraction $\Phi_a$ which can be estimated from the experimental data or mass balances.

The molar volume $v_m$ of the oil mixture can be calculated from the composition of the liquid phase obtained from vapor/liquid calculations provided by a suitable equation of state or other suitable method. The solubility parameter $\beta_m$ of the mixture can also be calculated from the equation of state or other suitable method. As mentioned earlier, all properties of asphaltenes are generally unknown—only a certain range is known as asphaltenes include a range of molecules from small polar molecules to large less polar molecules. Thus, the molar volume $v_a$ of asphaltene (which represents the ratio of molecular weight/density for the asphaltene) can be estimated if unknown. Hirschberg et al. used values of $v_a$ in the range of 1 to 4 m³/kmol. The solubility parameter of asphaltene $\delta_a$ can also be estimated if unknown. The experimental data derived from the solubility testing method and apparatus as described herein, which measures the solubility of asphaltene in a solvent-precipitant fluid of varying solvent volume fraction, can be used to estimate the molar volume $v_a$ and/or the solubility parameter of asphaltene $\delta_a$ if unknown.

Figure 10:
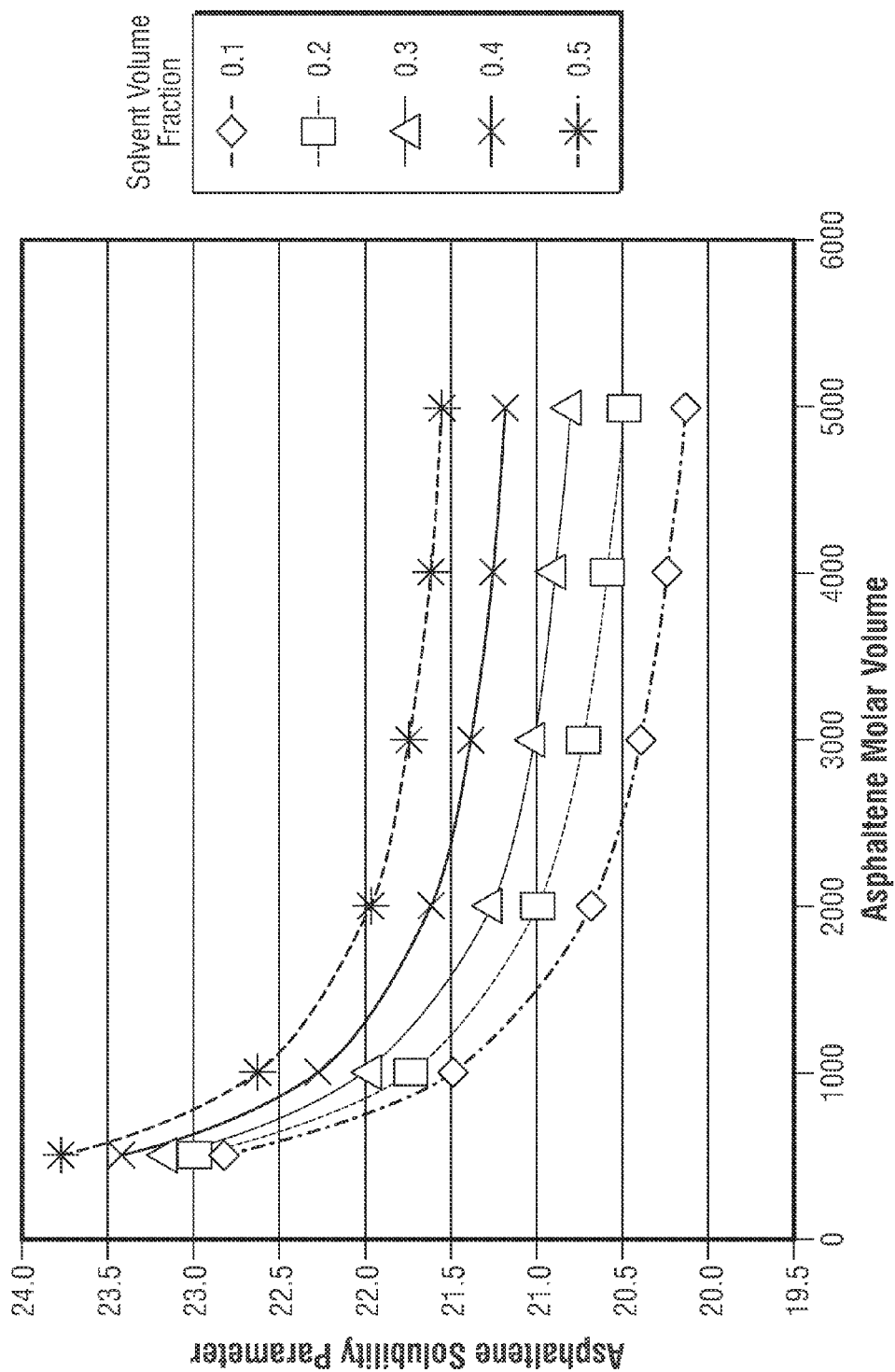
FIG. 10 is a graph showing the relationship of an asphaltene solubility parameter as a function of asphaltene molar volume calculated by solving a solubility model for a number of different mixtures (hydrocarbon sample/precipitant/solvent) of varying solvent volume fraction.
Figure 11:
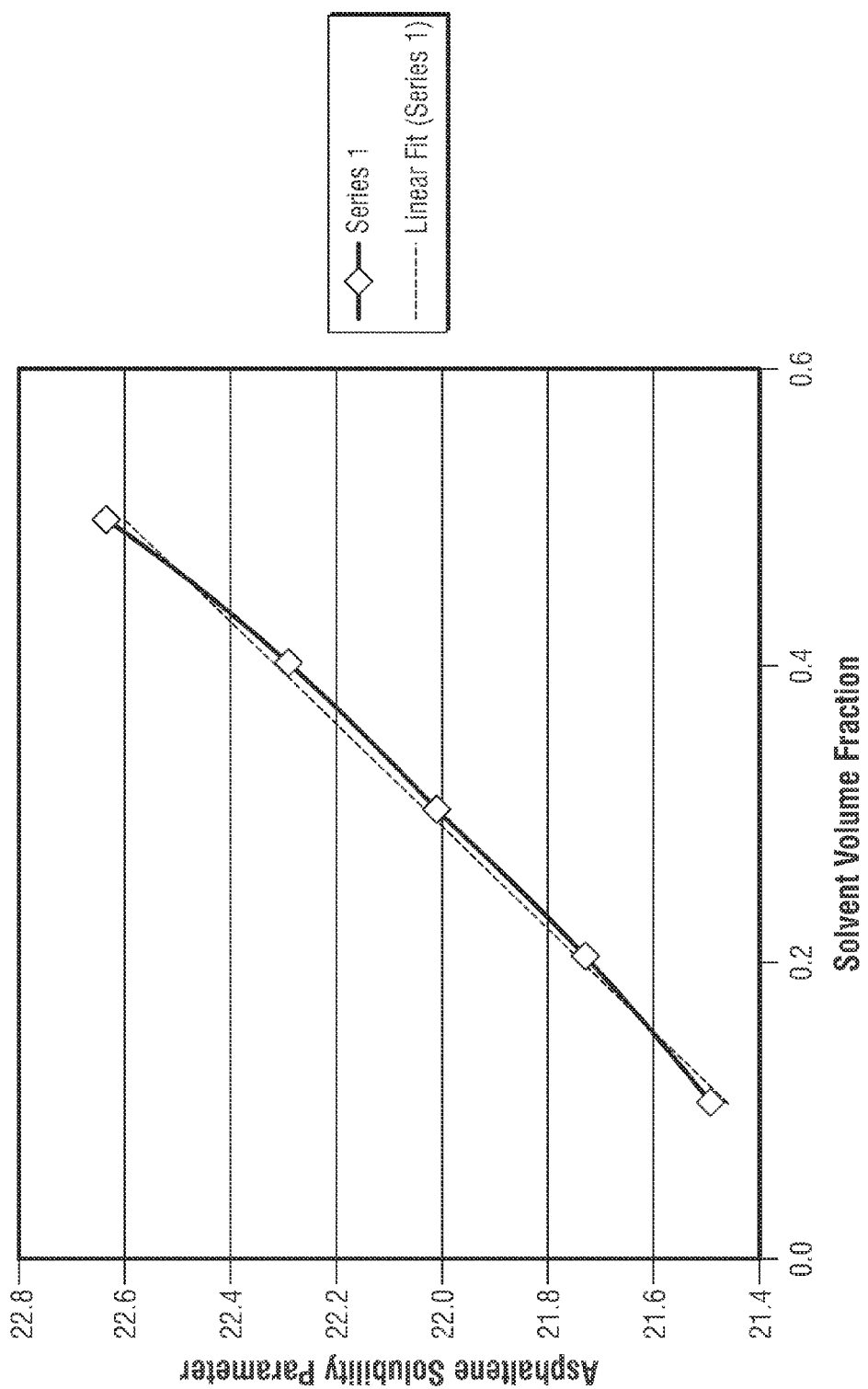
FIG. 11 is a graph including a number of data points and a best-fit function that relates an asphaltene solubility parameter to solvent volume fraction as calculated by solving a solubility model for a number of different mixtures of varying solvent volume fraction.
Figure 12:
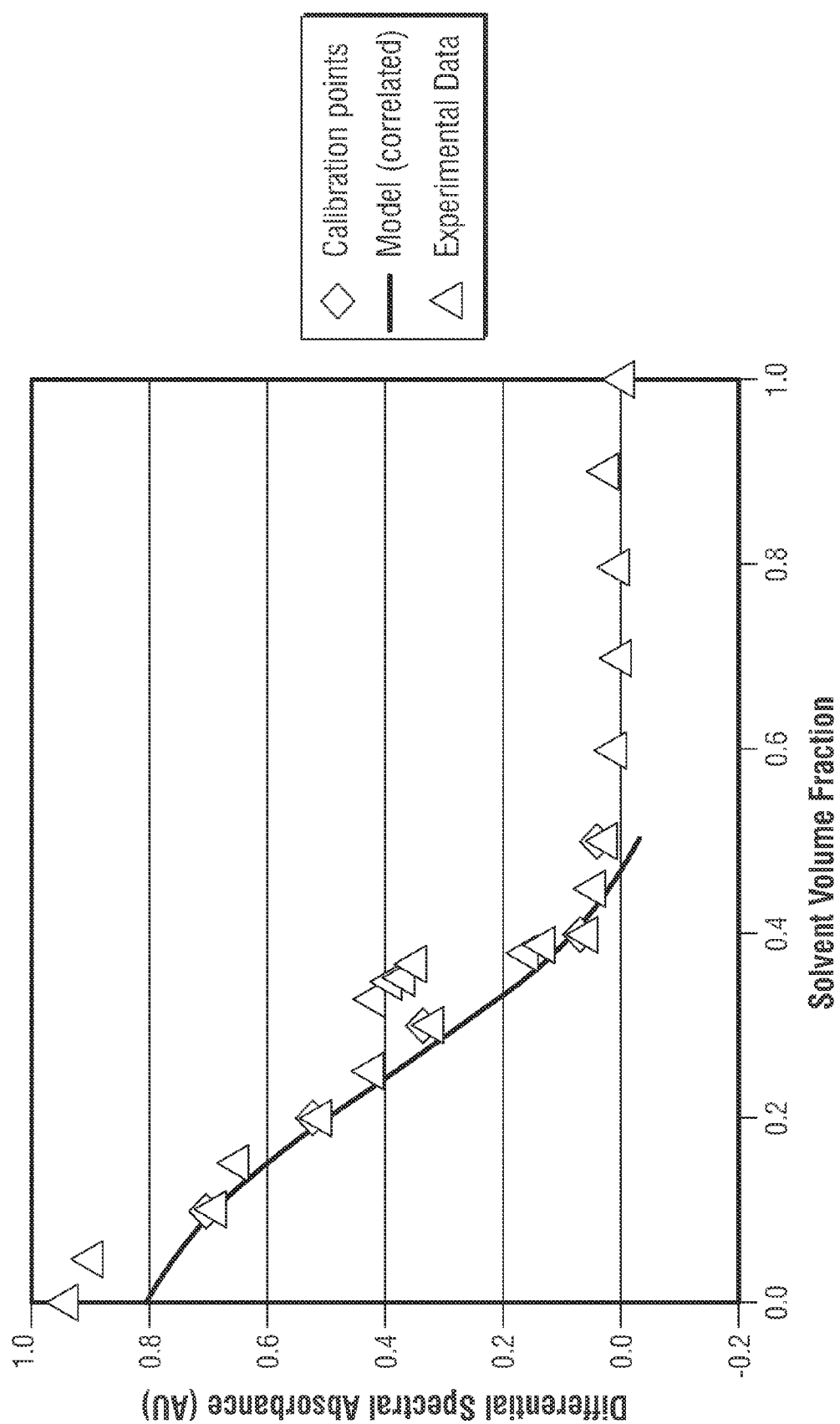
FIG. 12 is a graph including a number of experimental data points and a model correlated to the certain experimental data points that relate a differential spectral absorbance measurement to solvent volume fraction as calculated by solving a solubility model for a number of different mixtures of varying solvent volume fraction.

In one example, a correlation procedure can be used that varies molar volume of a number of experimental points and calculates the corresponding solubility parameter of asphaltene $\delta_a$ over a set of solvent-precipitant fluids of varying solvent volume fraction. Both the molar volume and the solubility parameter of the solvent can be used as input parameters while estimating the solubility parameter of the asphaltenes in solution. An example of the results of this correlation procedure is shown in FIG. 10. In this example, the correlation procedure followed the procedure outlined in Andersen and Stenby, "Thermodynamics of Asphaltene Precipitation and Dissolution Investigation of Temperature and Solvent Effects," *Fuel Science and Technology International*, Vol. 14, Iss. 1-2, 1996, herein incorporated by reference in its entirety. Note that for some oils, the results of the correlation procedure will yield a common point of intersection which then means one can model the system with one single pair of values for the asphaltene molar volume $v_a$ and the solubility parameter of asphaltene $\delta_a$. In the example shown in FIG. 10, there is no common point of intersection. Thus, any arbitrary value of asphaltene molar volume within the range of results (such as a value of 1000 cc/mole) can be selected. The model is in principle correct as it shows that as the solvent gets stronger only material with a higher solubility parameter precipitates. With more and more heptane in solution the value decreases indicating that more soluble asphaltenes are added to the precipitated material as the overall asphaltene solubility decreases toward "zero" at pure heptane. The latter cannot be modeled with the approach simply due to the thermodynamic framework and thus the pure heptane point is not used as a calibration point. However, it does define the actual solubility and can be calculated as a fraction of the total precipitated asphaltenes. Hence, the modeling is initialized by calculating the solubility parameter of asphaltene $\delta_a$ based on the difference between the amount of precipitated asphaltene in the precipitant alone (e.g., heptane) and the amount of precipitated asphaltene in a solvent/precipitant (e.g., toluene/heptane) mixture. FIG. 11 shows the results (labeled "Series 1") of such calculations over the set of solvent-precipitant fluids of varying solvent volume fraction. FIG. 11 also shows a best fit function (in this case, a line labeled "Linear Fit (Series 1)") that relates the solubility parameter of asphaltene $\delta_a$ to the solvent volume fraction of the mixture. This relation indicates that with one single molar volume, the average solubility parameter for all of the asphaltenes precipitating has to vary as the solvent power of the solvent phase is decreased in order to precipitate more asphaltene content as long as the solvent-hydrocarbon ratio is constant. Hence it represents a cumulative solubility parameter distribution related here to the solvent strength. This distribution can now be used to predict changes in both precipitant and solvents. In another example, the model can also be extended to relate the solubility parameter of asphaltenes $\delta_a$ to spectral absorbance as measured by a spectrometer) over the set of solvent volume fractions. The spectral absorbance as predicted by the model can be compared to experimental data and is directly related to the precipitated amount of asphaltenes at the given conditions. FIG. 12 shows a measure of differential spectral absorbance as predicted by the model (labeled "Model (correlated)") and corresponding experimental data measured by the test apparatus and method as described above over a set of solvent volume fractions. In this example, the molar volume of asphaltenes is set to 1000 cc/mole in the model.

Note that similar calculations can be performed with respect to other thermodynamic models that describe the phase behavior of asphaltene-containing hydrocarbon fluids. For example, a more complex model that treats asphaltenes as a molecular weight distribution with an independent solubility parameter (calibrated to density data if available from a crude oil characterization) is described in Sabbagh, O., Akbarzadeh, K., Badamchi-Zadeh, A., Svrcek, W. Y., and Yarranton, H. W., "Applying the PR-EoS to Asphaltene Precipitation from n-Alkane Diluted Heavy Oils and Bitumens," *Energy & Fuels* 2006, 20, pp. 625-634. The experimental data derived from the solubility testing method and apparatus as described herein can be used to estimate the molecular weight distributions and the independent solubility parameters of this more complex model. In other examples, thermodynamic models that describe the phase behavior of asphaltene-containing petroleum fluids can employ parameters that relate to the size of the asphaltene molecule, Hamaker constants for asphaltenes, and association energy parameters, all of which can be calibrated by the experimental data derived from the solubility testing method and apparatus as described herein.

Other thermodynamic models can be used to estimate diluent effect, blending of different oils, and the effects of injection gas or other fluids on asphaltene stability and yield. These thermodynamic models require a solubility parameter for asphaltenes, which can be estimated for a particular oil using the method and apparatus as described herein. For example, an oil compatibility model (OCM) can be used to predict the compatibility (or incompatibility) of any number of crude or processed oils. In this model, the critical solubility parameter $\delta_{cr}$ at which asphaltenes will reach incipient flocculation can be used to derive a flocculation solubility parameter called the insolubility number and the solubility parameter of the oil is called the solubility blending number. The criterion for oil compatibility is that the volume average solubility blending number of the mixture is higher than the insolubility number of any asphaltene-containing component in the mixture.

There have been described and illustrated herein several embodiments of an automated test apparatus and method that characterizes solubility of asphaltenes of a hydrocarbon sample that employs microfluidics. While particular embodiments have been described herein with reference to particular means, materials, and embodiments, it is not intended to be limited to the particulars described herein; rather it extends to all functionally equivalent structures and methods, such as are within the scope of the appended claims.

What is claimed is:

1. A method of analyzing solubility of asphaltenes of a hydrocarbon fluid sample, comprising:
    i) performing microfluidic mixing operations that form a mixture that includes a sample of the hydrocarbon fluid, a solvent fluid that dissolves asphaltenes, and a precipitant fluid that precipitates asphaltenes;
    ii) using microfluidic processes that can result in precipitation of asphaltenes from the mixture resulting from i);
    iii) performing microfluidic filtering operations that remove precipitated asphaltenes from the mixture that can result from ii) while outputting permeate;
    iv) performing optical spectroscopy on the permeate resulting from iii);
    v) repeating the operations of i)-iv) over a number of additional iterations that vary the amount of solvent fluid relative to the precipitant fluid in the mixture of i), wherein the iterations of i)-v) cause varying fractional precipitation of asphaltenes during the operations of ii) in each given iteration;
    vi) determining a value of spectral absorbance derived from the optical spectroscopy of iv) for each iteration i)-v); and
    vii) using the values of spectral absorbance for the iterations i)-v) as a function of the volume fractions of the solvent fluid in the mixtures of the iterations i)-v) to determine a solvent volume fraction for asphaltene flocculation onset with regard to the hydrocarbon fluid.

2. A method according to claim 1, further comprising:
    viii) performing microfluidic mixing operations that form a second mixture that includes a second portion of the hydrocarbon fluid sample and the solvent fluid, but does not include the precipitant fluid;
    ix) using microfluidic processes that result in dissolution of asphaltenes from the second mixture resulting from viii);
    x) performing microfluidic filtering operations that remove precipitated asphaltenes from the second mixture resulting from ix), if any, while outputting permeate; and
    xi) performing optical spectroscopy on the permeate resulting from x).

3. A method according to claim 2, further comprising:
    xii) performing microfluidic mixing operations that form a third mixture that includes a third portion of the hydrocarbon fluid sample and the precipitant fluid, but does not include the solvent fluid;
    xiii) using microfluidic reactions that result in precipitation of asphaltenes from the third mixture resulting from xii);
    xiv) performing microfluidic filtering operations that remove precipitated asphaltenes from the third mixture resulting from xiii) while outputting permeate; and xv) performing optical spectroscopy on the permeate resulting from xiv).

4. A method according to claim 1, wherein the microfluidic mixing operations of i), the microfluidic processes of ii), and the microfluidic filtering operations of iii) are performed by at least one microfluidic chip.

5. A method according to claim 4, wherein:
the at least one microfluidic chip comprises first and second input ports that are fluidly coupled to a mixer section;
the first input port is configured to supply a combination of the solvent fluid and the precipitant fluid to the mixer section for use in conjunction with the microfluidic mixing operations of i); and
the second input port is configured to supply the hydrocarbon fluid sample to the mixer section for use in conjunction with the microfluidic mixing operations of i).

6. A method according to claim 5, wherein the at least one microfluidic chip comprises a reactor section fluidly coupled downstream from the mixer section.

7. A method according to claim 6, wherein the at least one microfluidic chip comprises a membrane filter section fluidly coupled downstream from the reactor section, wherein the membrane filter section leads to both a waste port and an outlet port.

8. A method according to claim 4, wherein:
the microfluidic mixing operations of i) and the microfluidic processes of ii) are performed by a first microfluidic chip; and
the microfluidic filtering operations of iii) are performed by a second microfluidic chip that is separate and distinct from the first microfluidic chip and fluidly coupled to the first microfluidic chip.

9. A method according to claim 8, wherein a flow-through optical cell is fluidly coupled between the first microfluidic chip and the second microfluidic chip, and wherein the flow-through optical cell is optically coupled to a corresponding spectrometer.

10. A method according to claim 1, wherein the optical spectroscopy of iv) involves the permeate resulting from iii) passing through a flow-through optical cell, and wherein the flow-through optical cell is optically coupled to a corresponding spectrometer.

11. A method according to claim 1, wherein the operations of i) to iv) are part of an automated workflow involving automatic control of the flow rate of the hydrocarbon fluid sample, the solvent fluid, and the precipitant fluid that is mixed in i) and automatic control of the optical spectroscopy of iv).

12. A method according to claim 1, wherein the iterations of the operations of i) to iv) are part of an automated workflow involving automatic control of the flow rate of the hydrocarbon fluid sample, the solvent fluid, and the precipitant fluid that is mixed in i) during each given iteration and automatic control of the optical spectroscopy of iv) during each given iteration.

13. A method according to claim 1, wherein the hydrocarbon fluid sample is selected from the group consisting of a crude oil sample, a blend of different crude oils, one or more additives combined with crude oil, coal liquefaction products, mixtures of naphtha and bitumen, mixtures of refinery residua and diluents, and road asphalts.

14. A method according to claim 1, further comprising:
deriving and storing an optical spectrum measurement during the optical spectroscopy of iv) for each given iteration; and
processing the stored optical spectrum measurement in order to derive experimental data related to a solvent volume fraction of the mixture for each given iteration.

15. A method according to claim 14, further comprising:
using the experimental data to tune a model that describes the phase-behavior of asphaltene-containing petroleum fluids.

16. A method according to claim 14, further comprising:
using the experimental data to derive at least one of a solubility blending number and an insolubility number for the hydrocarbon sample.

17. A method according to claim 16, wherein:
the solubility blending number and the insolubility number of the hydrocarbon sample are used as a criterion for oil compatibility of a mixture, wherein the criterion involves comparing the volume average solubility blending number of the components of the mixture and the insolubility number of any asphaltene-containing component of the mixture.

18. A method according to claim 1, wherein:
the solvent fluid is selected from the group consisting of toluene, dichloromethane (DCM), xylenes, benzene, methyl naphthalene, cyclohexane, tetrahydrofuran (THF), chloroform, trichloroethylene, tetrachloroethylene, carbon tetrachloride, carbon, and other fluids that dissolve asphaltenes.

19. A method according to claim 1, wherein:
the precipitant fluid is selected from the group consisting of n-heptane, n-pentane, n-hexane, petroleum ether, ethyl acetate, alcohols, and other fluids that precipitate asphaltenes.

20. A method according to claim 1, further comprising:
viii) using the solvent volume fraction for asphaltene flocculation onset determined in vii) to calculate a solubility parameter of asphaltenes for the hydrocarbon fluid.

21. A method according to claim 20, wherein:
the solubility parameter of asphaltenes for the hydrocarbon fluid is calculated from the solvent volume fraction for asphaltene flocculation onset in viii) according to the relation $$\delta_{cr} = R_{fo} * (\delta_s - \delta_p) + \delta_p,$$

where $\delta_{cr}$ is solubility parameter of asphaltenes for the hydrocarbon fluid,
$R_{fo}$ is the solvent volume fraction for asphaltene flocculation onset determined in vii),
$\delta_s$ is a solubility parameter for the solvent fluid, and
$\delta_p$ is q solubility parameter of the precipitant fluid.

22. A method according to claim 1, wherein:
the value of spectral absorbance determined in vi) for each iteration i)-v) is based on a difference in spectral absorbance of the hydrocarbon sample over multiple wavelengths of an optical spectrum derived from performing the optical spectroscopy in iv).

23. A method according to claim 2, wherein:
the value of spectral absorbance determined in vi) for each iteration i)-v) is adjusted by a difference in spectral absorbance of the hydrocarbon sample over multiple wavelengths of an optical spectrum derived from performing optical spectroscopy in xi).

24. A method according to claim 2, wherein:
the value of spectral absorbance determined in vi) for each iteration i)-v) is based on a difference in spectral absorbance of the hydrocarbon sample over multiple wavelengths of an optical spectrum derived from performing the optical spectroscopy in iv), and is adjusted by a difference in spectral absorbance of the hydrocarbon sample over multiple wavelengths of an optical spectrum derived from performing optical spectroscopy in xi).

25. A method according to claim 1, wherein:
the function of vii) comprises a linear function that best fits the values of spectral absorbance for the iterations i)-v) and the volume fractions of the solvent fluid in the mixtures of the iterations i)-v); and
the solvent volume fraction for asphaltene flocculation onset is equated to the x-intercept of the linear function in viii).

* * * * *